US008404650B2

(12) United States Patent
Koch et al.

(10) Patent No.: US 8,404,650 B2
(45) Date of Patent: Mar. 26, 2013

(54) METHODS OF TREATING CANCER WITH DOXAZOLIDINE AND PRODRUGS THEREOF

(75) Inventors: Tad H. Koch, Boulder, CO (US); David J. Burkhart, Spokane Valley, WA (US); Glen C. Post, Spokane, WA (US); Jordan W. Nafie, Jupiter, FL (US); Brian T. Kalet, Sunvalley, NV (US); Benjamin L. Barthel, Broomfeld, CO (US); Daniel L. Rudnicki, Golden, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 678 days.

(21) Appl. No.: 12/091,321

(22) PCT Filed: Oct. 30, 2006

(86) PCT No.: PCT/US2006/060367
§ 371 (c)(1),
(2), (4) Date: Dec. 20, 2010

(87) PCT Pub. No.: WO2007/102888
PCT Pub. Date: Sep. 13, 2007

(65) Prior Publication Data
US 2011/0135618 A1      Jun. 9, 2011

Related U.S. Application Data
(60) Provisional application No. 60/731,323, filed on Oct. 28, 2005.

(51) Int. Cl.
*A01N 43/04* (2006.01)
*A61K 31/70* (2006.01)
(52) U.S. Cl. ............................. 514/34; 514/25; 514/35
(58) Field of Classification Search ........................ None
See application file for complete search history.

(56) References Cited

U.S. PATENT DOCUMENTS

| | | | |
|---|---|---|---|
| 6,214,345 | B1 | 4/2001 | Firestone et al. |
| 6,677,309 | B1 | 1/2004 | Taatjes et al. |
| 2003/0068792 | A1 | 4/2003 | Chen et al. |

OTHER PUBLICATIONS

Written Opinion for International (PCT) Patent Application No. PCT/US2006/060367, mailed Feb. 22, 2008.
International Preliminary Report on Patentability for International (PCT) Patent Application No. PCT/US2006/060367, mailed May 8, 2008.
Fenick, at. al., Doxoform and Daunoform: Anthracycline-Formaldehyde Conjugates Toxic to Resistant Tumor Cells; Journal of Medicinal Chemistry (1997); vol. 40, No. 16, pp. 2452-2461.
De Groot, et. al.; Elongated Multiple Electronic Cascade and Cyclization Spacer Systems in Activatable Anticancer Prodrugs for Enhanced Drugs Release; Journal of Organic Chemistry (2001), vol. 66, pp. 8815-8830.
International Search Report prepared by the U.S. Patent and Trademark Office on Jan. 12, 2008 for PCT/US2006/060367; Applicant, The Regents of The University of Colorado.
De Groot, et al., "Design, Synthesis, and Biological Evaluation of a Dual Tumor-specific Motive Containing Integrin-targeted Plasmin-cleavable Doxorubicin Prodrug", Molecular Cancer Therapeutics, Sep. 2002, pp. 901-911, vol. 1.
De Groot, et al;, "Elongated Multiple Electronic Cascasde and Cyclization Spacer Systems in Activatible Anticancer Prodrugs for Enhanced Drug Release", J. Org. Chem., 2001, pp. 8815-8830, vol. 66, No. 26.
Devy, et al., "Plasmin-activated doxorubicin prodrugs containing a spacer reduce tumor growth and angiogenesis without systemic toxicity", The FASEB Journal, 2004, Published on-line Jan. 20, 2004, pp. 565-567, vol. 18.
Niculescu-Duvaz, et al., "Significant differences in biological parameters between prodrugs cleavable by carboxypeptidase G2 that generate 3,5-difluoro-phenol and -aniline nitrogen mustards in gene-directed enzyme prodrug therapy systems", J. Med. Chem., May 6, 2004, pp. 2651-2658, vol. 47.
Hudyma, et al., "Synthesis and release of doxorubicin from a cephalosporin based prodrug by a β-lactamase-immunoconjugate", Bioorganic & Medical Chemistry Letters, 1993, pp. 323-328, vol. 3, Issue 2.
Cortez-Retamozo, et al., "Efficient Cancer Therapy with a Nanobody-Based Conjugate", Cancer Research, Apr. 15, 2004, pp. 2853-2857, vol. 64.
Sharma, et al., "Sustained Tumor Regression of Human Colorectal Cancer Xenografts Using a Multifunctional Mannosylated Fusion Protein in Antibody-Directed Enzyme Prodrug Therapy", Clinical Cancer Research, Jan. 15, 2005, pp. 814-825, vol. 11.
Sharma, et al., "Human Immune Response to Monoclonal Anti-body-Enzyme Conjugates in ADEPT Pilot Clinical Trial", Cell Biophysics, 1992, pp. 109-120, vol. 21, Humana Press Inc.
Xu, et al., "Strategies for Enzyme/Prodrug Cancer Therapy", Clinical Cancer Research, Nov. 2001, pp. 3314-3324, vol. 7.
Lampidis, et al., "Circumvention of P-GP MDR as a Function of Anthracycline Lipophilicity and Charge", Biochemistry, 1997, pp. 2679-2685, vol. 36.
Rona, et al., "The Reaction of β-Hydroxyalkylcarbamates with Carbonyl Compounds", J. Org. Chem., 1961, pp. 1446-1450, vol. 26.
Fennick, et al., "Doxoform and Daunoform: Anthracycline-Formaldehyde Conjugates Toxic to Resistant Tumor Cells", Journal of Medicinal Chemistry, 1997, pp. 2452-2461, vol. 40, No. 16.

*Primary Examiner* — Jeffrey S. Lundgren
*Assistant Examiner* — Michael Schmitt
(74) *Attorney, Agent, or Firm* — Sheridan Ross P.C.

(57) ABSTRACT

The invention provides therapeutically effective compounds for the prevention and treatment of cancer and pharmaceutical compositions containing these compounds as well as methods of using and administering these compounds. The invention also includes methods of activating a prodrug of these therapeutically effective compounds by the administration of a peptide-directed targeting construct that delivers a prodrug-activating enzyme to a target activation site.

9 Claims, 10 Drawing Sheets

METHODS OF TREATING CANCER WITH DOXAZOLIDINE AND PRODRUGS THEREOF

CROSS REFERENCE TO RELATED APPLICATIONS

This application is a national stage application under 35 U.S.C. 371 of PCT Application No. PCT/US2006/060367 having an international filing date of Oct. 30, 2006, which designated the United States, which PCT application claimed the benefit of U.S. Application Ser. No. 60/731,323, filed Oct. 28, 2005, the entire disclosure of each of which is incorporated herein by reference.

GOVERNMENT INTEREST

This invention was made with Government support under CA92107 awarded by the National Institutes of Health (NIH) and DAMD17-01-1-0046 awarded by the U.S. Army Research Office. The Government has certain rights in the invention.

FIELD OF THE INVENTION

The invention relates to anthracycline anti-tumor compounds and method of treating cancers using these compounds. Specifically, the invention provides anti-tumor compounds having greater cytotoxicity than doxorubicin as well as enzymatically-activated prodrugs of these compounds and methods of synthesizing and using these anti-tumor compounds in the treatment of patients with cancer and neoplastic growth.

BACKGROUND OF THE INVENTION

Doxorubicin (FIG. 1) is a broad-spectrum anthracycline, anti-tumor drug used for the treatment of leukemias, lymphomas and solid tumors and is a main-line drug for the treatment of breast cancer. Unfortunately, Doxorubicin exhibits frequent and dose-limiting or even drug-limiting cardiotoxicity. Additionally, most multidrug-resistant tumors and cancer cells display resistance to Doxorubicin. While these undesirable characteristics have limited the clinical usefulness of Doxorubicin, the drug remains one of the oldest and most used anthracycline anti-tumor compounds due to its substantial toxicity to sensitive cancer cells. For this reason, there has been an intensive search for similar anthracycline compounds or derivatives of Doxorubicin having the same or similar anti-tumor activity with greater specificity and/or activity in drug-resistant neoplastic cells.

Research into the mechanism of action of Doxorubicin led to the discovery of the potent formaldehyde Doxorubicin derivative, Doxoform (DoxF, FIG. 1 and U.S. Pat. No. 6,677, 309) which cross-links nuclear and mitochondrial DNA and inhibits equally the growth of sensitive and multidrug-resistant cancer cells. DoxF has shown substantial anti-tumor activity (approximately 100-fold above Doxorubicin) that is attributable to the oxazolidine ring formed by the reaction of Doxorubicin with formaldehyde. Additionally, DoxF is no more toxic to cardiomyocytes than Doxorubicin itself. Unfortunately, DoxF is highly susceptible to hydrolysis and therefore, relatively unstable.

The discovery and characterization of the molecular events leading to the cross-linking of DNA by anthracycline drugs, including the induction of formaldehyde synthesis and its role in DNA cross-link formation, led to the synthesis of Daunoform from daunorubicin (FIG. 2), and Epidoxoform (EpiF, FIG. 3) from epidoxorubicin (FIG. 2). Evaluation of these compounds in tissue culture and mice revealed that, although these conjugates have dimeric structures, they function as prodrugs for the monomeric formaldehyde conjugates that cross-link DNA. EpiF differs in structure from DoxF by having the formaldehyde incorporated in 7-membered rings rather than 5-membered rings because of a difference in stereochemistry at the amino sugar. Early on, EpiF was selected as the lead compound because of its stability in water with respect to loss of formaldehyde (half-life 2 hours). While EpiF proved to be more active than epidoxorubicin in cancer cell growth inhibition and in a murine breast tumor model, it was 50-fold less active than DoxF in cancer cell growth inhibition.

The second lead compound, doxsaliform (DoxSF, FIG. 1), contained the formaldehyde as an N-Mannich base with salicylamide and had a monomeric structure rather than a dimeric structure. The N-Mannich base served as a time-release device (half-life 1 hour) for the Doxorubicin-formaldehyde Schiff base (FIG. 3). It also provided functionality for attaching targeting groups that could direct the construct to receptors overexpressed by tumor cells and their associated angiogenesis. DoxSF was also more effective at tumor cell growth inhibition than Doxorubicin but again 50-fold less active than DoxF.

Additional studies have attempted to use methods of targeting prodrugs of Doxorubicin to tumor cells to increase the specificity of these drugs, thereby reducing the non-specific toxicity and related side effects. Antibody Directed Enzyme Prodrug Therapy (ADEPT) and Gene Directed Enzyme Prodrug Therapy (GDEPT) were promising methods for tumor localization of a prodrug-activating enzyme that have been studied over the past six years for anthracycline-based drugs, and particularly Doxorubicin, as Doxorubicin is a widely-used anti-tumor agent that is relatively easy to derivatize. The most effective Doxorubicin prodrugs to utilize this enzyme-activated approach incorporated a peptide or sugar recognized and cleaved by endogenous or non-native-enzymes near the tumor or its supporting vasculature with the goal of reducing the dose-limiting cardiotoxic side effect of Doxorubicin.

Scheeren and coworkers (Mal. Cancer Therap., 1: 901-911, 2002; J. Org. Chem., 2001: 8815-8830, 2001) developed a plasmin-activated tripartate Doxorubicin prodrug, ST-9802, with reduced cardio and systemic toxicity. Plasmin is a protease over-expressed by numerous cancer types and, although it is found in the bloodstream, its activity is inhibited by α2-antiplasmin and α2-macroglobulin. ST-9802 showed no release of Doxorubicin after incubation in bovine serum for 3 days, indicating good plasmin specificity. While the toxicity of ST-9802 was reduced, some efficacy was lost as well and it failed to match the tumor growth inhibition of Doxorubicin in mice bearing human MCF-7 breast tumors even at an equi-toxic dose. A variant of ST-9802 with an elongated Katzenelenbogen-type spacer ST-9905 fared better in mouse efficacy experiments, but at best could only match the activity of Doxorubicin (FASEB J., 18: 565-567, 2004).

In 2004 Springer and co-workers (J. Med. Chem., 47: 2651-2658, 2004) reported on a series of nitrogen mustard prodrugs activated by carboxypeptidase G2 (CPG2) produced by *Pseudomonas aeruginosa* type RS16. These prodrugs were designed to be activated in vivo by the prior administration of a tumor-specific monoclonal antibody conjugated to CPG2. These nitrogen mustard prodrugs have been evaluated using both ADEPT and GDEPT strategies and one of these compounds, ZD2767, showed significant tumor growth inhibition in mice.

In related studies, the capacity of β-lactamase enzymes from *Enterobacter* species to selectively hydrolyze the β-lactam ring of cephalosporins and penicillins was used to activate a number of cytotoxin-containing prodrugs (Bioorg. Med. Chem. Lett., 3: 323-328, 1993; Cancer Res., 64: 2853-2857, 2004). When used in conjunction with numerous antibody/β-lactamase enzyme conjugates, the Doxorubicin-cephem prodrug achieved higher intratumoral levels of Doxorubicin and exhibited tumor growth inhibition comparable to Doxorubicin.

Although groundbreaking in their day, these prodrug designs failed to address the issue of drug resistance since they relied on Doxorubicin for their cytotoxic effect and several resistance mechanisms for Doxorubicin are known. Since Doxorubicin is a cation at physiological pH, its capacity to diffuse is limited and, therefore, its bystander effect modest. Indeed, none of the Doxorubicin-containing prodrugs described above outperformed Doxorubicin in mouse xenograft assays.

Although ADEPT has advanced significantly, and even landed a few prodrugs in clinical trials, there is still substantial room for improvement. As antibodies are large molecules (approx. 150 kDa) and therefore diffuse very slowly, they are poor targeting agents for many solid tumors. Due to important advances in protein engineering, recombinant fragments that retain most of the antigen affinity and are significantly smaller (approx. 25 kDa) have been made, but these antibodies still need to be humanized to reduce immunogenic response in the host. Immune response to antibody reduces the effectiveness of therapy by removing the antibody-enzyme conjugate from circulation before it reaches the tumor and often limits therapy to a single ADEPT cycle. In addition, humanized antibody development is expensive and time consuming, and constructs containing enzymes often have significantly-reduced enzymatic activity, ands antibody-enzyme conjugates are large molecules that are slow to penetrate tumors, if they do so at all.

Therefore, there is a need for a novel approach to antitumor drug targeting that is quick, efficient, and involves a small molecule as a targeting group. Preferably, such a prodrug approach could incorporate the anti-tumor efficacy of doxorubicin while eliminating, or substantially reducing, the associated cardiotoxicity and simultaneously overcoming the doxorubicin drug resistance displayed by many cancer cells.

SUMMARY OF THE INVENTION

The present invention provides highly cytotoxic derivatives of doxorubicin for use as anti-cancer compounds and prodrugs thereof. These compounds and the prodrugs have been designed to target and efficiently kill tumor cells with at least as much efficacy as doxorubicin while simultaneously increasing the bystander effect while reducing the cardiotoxicity of doxorubicin. Additionally, these anti-cancer compounds overcome most or all of the drug resistance displayed to doxorubicin by many cancer cells. The novel derivatives of doxorubicin that have been designed, synthesized and evaluated by the present inventors and are disclosed herein include doxorubicin-formaldehyde conjugates having an oxazolidine ring.

These conjugates may be formulated as prodrugs by forming a carbamate with the doxorubicin-formaldehyde conjugate having one or more carbamate groups. These prodrugs are activated by the action of carboxylesterases to hydrolyze the terminal carbamate to carbamic acid.

Alternatively, these conjugates may be formulated as prodrugs by forming a carbamate linked to a peptide that is a target for enzyme cleavage through a N-L-leucyl linkage. Enzymatic cleavage of the target peptide sequence releases the active doxorubicin-formaldehyde conjugate. The enzyme target may be chosen to be cleaved by an enzyme associated with tumor cells such as plasmin or prostate specific antigen.

Similarly, these conjugates may be formulated as prodrugs by forming a carbamate linked to a peptide that is a target for enzyme cleavage through at least one p-aminobenzyloxycarbonyl (PABC) spacer. Preferably, the enzyme target of these prodrugs is chosen to be plasmin. Similarly, these conjugates may be formulated as prodrugs by forming a carbamate linked to glucuronic acid that is a target for enzyme cleavage through a p-aminobenzyloxycarbonyl (PABC) spacer. The enzyme target of these prodrugs is beta-glucuronidase. Alternatively, these conjugates may be formulated as prodrugs by forming a carbamate linked to a beta-lactam antibiotic that is a target for enzyme cleavage. The enzyme target of these prodrugs is a beta-lactamase.

These conjugates may be formulated as prodrugs by forming a urea linked to glutamic acid that is a target for enzyme cleavage through a p-aminobenzyloxycarbonyl (PABC) spacer. The enzyme target of these prodrugs is a carboxyglutamase.

These doxorubicin-formaldehyde conjugates and the prodrugs thereof are useful for treating cancer or inhibiting the growth of cancer cells in mammals. These conjugates are also useful in cross-linking DNA. Thus, related embodiments of the present invention include the use of these conjugates, or pharmaceutically-acceptable salts thereof, for the treatment or inhibition of cancer growth and/or the cross-linking of DNA. These conjugates may be used directly in vitro or in cell culture or may be formulated as a pharmaceutically-acceptable dosage form in combination with any necessary or desired pharmaceutical excipients for ease of administration to a mammal in need of such treatment. The appropriate dosage to be administered to a patient will be a therapeutically-effective amount that is determined by a physician.

BRIEF DESCRIPTION OF THE DRAWINGS

FIG. 8A shows the synthesis of a Doxaz prodrug with the oxazolidine ring protected as carbamate, one PABC spacer, and a plasmin cleavage site. FIG. 8B depicts the synthesis of a plasmin-activated Doxaz prodrug with the oxazolidine ring protected as carbamate, two PABC spacers and a plasmin cleavage site. The constructs have good water solubility due to the di-cationic D-Ala-L-Phe-L-Lys peptide. The abbreviations used in this Figure are: alloc, allyloxycarbonyl; Boc, t-butyloxycarbonyl; DIEA, di-isopropylethylamine; DMF, dimethylformamide; HOBt, 1-hydroxybenzotriazole; TFA, trifluoroacetic acid; THF, tetrahydrofuran; TIS, tri-isopropylsilane.

DETAILED DESCRIPTION OF THE INVENTION

Figure 1:
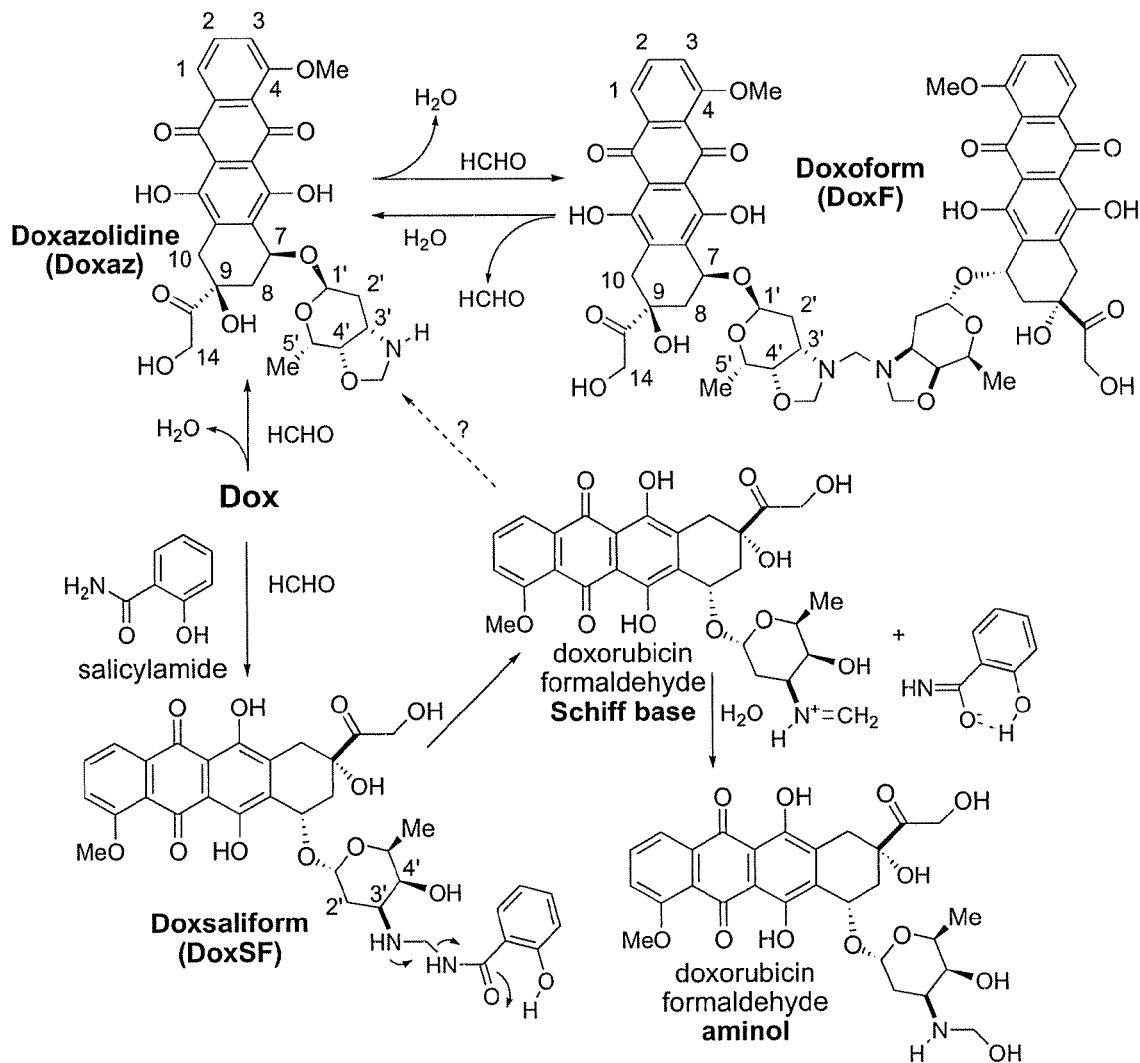
FIG. 1 shows synthesis of Doxoform (DoxF) and Doxsaliform (DoxSF) from Doxorubicin and their partial hydrolysis to Doxazolidine (Doxaz) and doxorubicin-formaldehyde conjugates (Schiff base or aminol).

The present invention is drawn to compounds that exhibit significant anti-cancer activity against solid tumors, cancers and neoplastic cells with reduced cardiotoxicity and susceptibility to the mechanisms of elimination by multidrug-resistant cancer cells.

A. Doxazolidine

It has been discovered by the present inventors that Doxoform (DoxF) is a prodrug for the monomeric doxorubicin oxazolidine, Doxazolidine (Doxaz), and that Doxaz is more reactive than acyclic conjugates in cross-linking DNA. The synthesis, isolation, and characterization of Doxaz as well as kinetics for hydrolysis of DoxF to Doxorubicin via Doxaz, and in vitro activity of Doxaz against sensitive and resistant cancer cells are described in Example 1 of this disclosure.

Doxaz inhibits the growth of tumor cells significantly better than Doxsaliform (DoxSF), Epidoxoform (EpiF), Epidoxorubicin (Epi), or Doxorubicin. Of particular significance is the higher activity of Doxaz relative to DoxSF, which is a prodrug for an acyclic Doxorubicin-formaldehyde conjugate such as the Schiff base or aminol. Doxaz contains a formaldehyde equivalent in a more stable oxazolidine ring than does Doxorubicin aminol or Schiff base. Doxaz is not a cation at physiological pH and consequently, is more lipophilic than Doxorubicin and better able to overcome P-170 glycoprotein drug efflux pump responsible for the multi-drug resistant phenotype. Additionally, Doxaz is fast acting and can rapidly form virtual cross-links to DNA such that it is not accessible to the efflux pump.

As described above and shown in Example 1, the reaction of formaldehyde with Doxorubicin forms an oxazolidine ring, producing the highly cytotoxic Doxorubicin derivative, Doxaz, Doxf, and correspondingly Doxaz, cross-link DNA resulting in apoptotic as well as non-apoptotic cancer cell death. Doxaz is 10-100 fold more toxic to a wide variety of sensitive cancer cells than Doxorubicin. Additionally, Doxaz is 500-10,000 fold more toxic to a variety of multidrug-resistant cancer cells than Doxorubicin. In spite of its drastically increased toxicity to cancer cells, Doxaz is no more cardiotoxic than Doxorubicin when assayed in rat cardiomyocytes. Further, circumstantial data link Doxaz to a 75% improvement relative to Doxorubicin in a clinical trial for the treatment of liver cancer. Doxaz is also uncharged and lipophilic and consequently able to overcome drug resistant phenotypes conferred by the P-170 glycoprotein drug efflux pump because, unlike Doxorubicin, it is not a cation at physiological pH. Thus, Doxaz fulfils the need for an anthracycline anti-cancer drug that overcomes drug resistance displayed by many cancer cells.

Doxaz is useful for the treatment of cancer and neoplastic cells or tissues including solid tumors. These conjugates are also useful in cross-linking DNA in vivo, in vitro, or in situ (particularly in cell culture). Thus, one embodiment of the present invention is the use of Doxaz to treat or inhibit the growth of cancer. A related embodiment is the use of Doxaz for the cross-linking of DNA. Doxaz may be used directly in vitro or in cell culture. Additionally Doxaz may be formulated as a pharmaceutically acceptable dosage form in combination with any necessary or desired pharmaceutical excipients for ease of administration to a mammal in need of such treatment. The appropriate dosage to be administered to a patient will be a therapeutically-effective amount that is determined by a physician.

Figure 2:
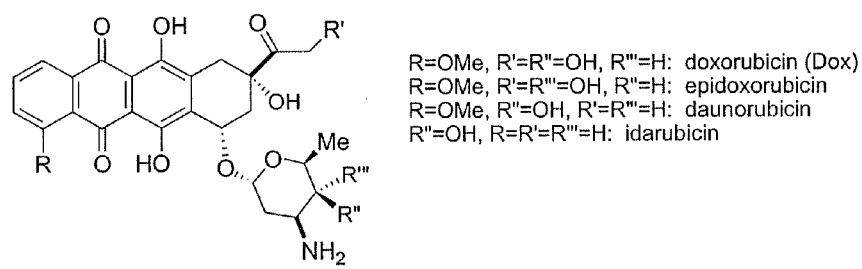
FIG. 2 shows the structures for doxorubicin and its clinical congeners: epidoxorubicin, daunorubicin, and idarubicin.

The results presented in Example 1 of this disclosure show that the formaldehyde conjugate of Epidoxorubicin (Epi), Epidoxoform (EpiF), is an order of magnitude less active at inhibiting tumor cell growth than is DoxF, even though Epi is only slightly less active than Doxorubicin. Like DoxF, EpiF has a dimeric structure from reaction of two Epi molecules with three formaldehyde molecules; however, because of the trans stereochemistry of the vicinal amino alcohol, the structure is bicyclic with 7-membered rings. It also virtually cross-links DNA, and the crystal structure of the cross-link is very similar to that formed with daunorubicin (shown in FIG. 2). Upon hydrolysis, EpiF slowly forms a monomeric species with one formaldehyde attached as an aminol. An aminol structure is also proposed for the intermediate from partial hydrolysis of DoxSF. Thus, an anthracycline-formaldehyde conjugate that has an oxazolidine ring, or releases a derivative with an oxazolidine ring, inhibits the growth of tumor cells much better than an anthracycline-formaldehyde conjugate that releases a derivative with the formaldehyde incorporated as an aminol.

B. Prodrugs of Doxazolidine

A related embodiment of the present invention is a prodrug of an anthracycline-formaldehyde conjugate that has an oxazolidine ring. The prodrug compound of this embodiment releases an anthracycline-formaldehyde conjugate with an oxazolidine ring. Preferably, the oxazolidine ring of this conjugate is unsubstituted. These conjugates are also useful for the treatment or inhibition of growth of cancer in mammals requiring such treatment and in cross-linking DNA. Thus, related embodiments of the present invention include the use of a prodrug of an anthracycline-formaldehyde conjugate that has an oxazolidine ring for treating or suppressing the growth of cancer and/or the cross-linking of DNA. These conjugates may be used directly in vitro or in cell culture or may be formulated as a pharmaceutically acceptable dosage form in combination with any necessary or desired pharmaceutical excipients for ease of administration to a mammal in need of such treatment.

An effective tumor-activated prodrug should distribute efficiently to tumor tissue and undergo selective metabolism at the site of the tumor site to release the cytotoxic species. The active drug must then survive diffusion to neighboring tumor cells that cannot activate prodrug. This "bystander effect" is of great importance in prodrug therapy because only a small percentage of tumor cells will be capable of activating prodrug. As a general rule, the more lipophilic a drug is, the more likely it is to display a significant bystander effect due to its increased rate of diffusion through membranes. Due to the importance of diffusion, a prodrug that is activated extracellularly has a significant advantage, in that its effect is not isolated to one cell but rather has the potential to act on neighboring cells. Finally, the active form of the prodrug should have a very short lifetime (from many seconds to a few minutes) so the highly cytotoxic component cannot spread to normal tissue. Doxaz possesses each of these characteristics of lipophilicity, potent cytotoxicity, and short half-life, making it an outstanding prodrug. But Doxaz suffers from low water solubility and instability in aqueous media (half-life of approximately 3 min at 37° C. for hydrolysis to Doxorubicin) due to the hydrolytically-sensitive oxazolidine ring. A prodrug form could vastly improve its water solubility and aqueous instability by protecting the oxazolidine ring. Thus, the chemical characteristics and physiological anti-cancer activity of Doxaz all point to the successful design of an active chemotherapeutic compound perfectly suited to formulation as a prodrug.

Novel Doxaz prodrug compounds that are enzymatically activated to release the active DNA-cross-linking anti-cancer compound Doxaz have been designed, synthesized and evaluated. These prodrugs use a carbamate functional group to protect the sensitive oxazolidine nitrogen of Doxaz, proffering greater stability, water solubility, and tumor selectivity. These Doxaz-carbamate compounds exhibit the potent anti-cancer activity of free Doxaz with the reduced cardiotoxicity expected of Doxaz prodrugs. Three strategies are relied upon for the activation of these prodrugs; 1) activation by native enzymes expressed at higher levels within cancer cells, 2) activation by native enzymes at the tumor via Antibody Directed Enzyme Prodrug Therapy (ADEPT), and 3) activation by a novel Peptide Directed Enzyme Prodrug Therapy (PeDEPT).

1. Doxazolidine Carbamates

Carbamate-protected Doxazolidine derivatives were designed for the treatment of primary and metastatic liver cancer. Doxoform, a prodrug of Doxazolidine, has $IC_{50}$ values for the inhibition of Hep-G2 and SK-HEP-1 human liver cancer cells more than 25-fold lower than doxorubicin. Enzymatic release of Doxazolidine from its carbamate in the liver by carboxylesterases (depicted in FIG. 6) coupled with the short half-life of Doxazolidine provides an effective strategy for targeted treatment of liver cancer.

One particularly useful prodrug of the present invention is a carbamate of doxazolidine having the chemical structure of Formula I:

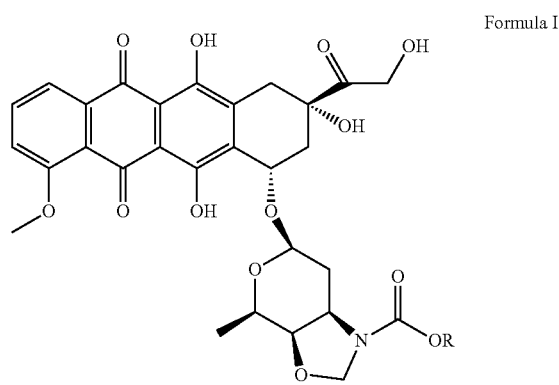

Figure 6:
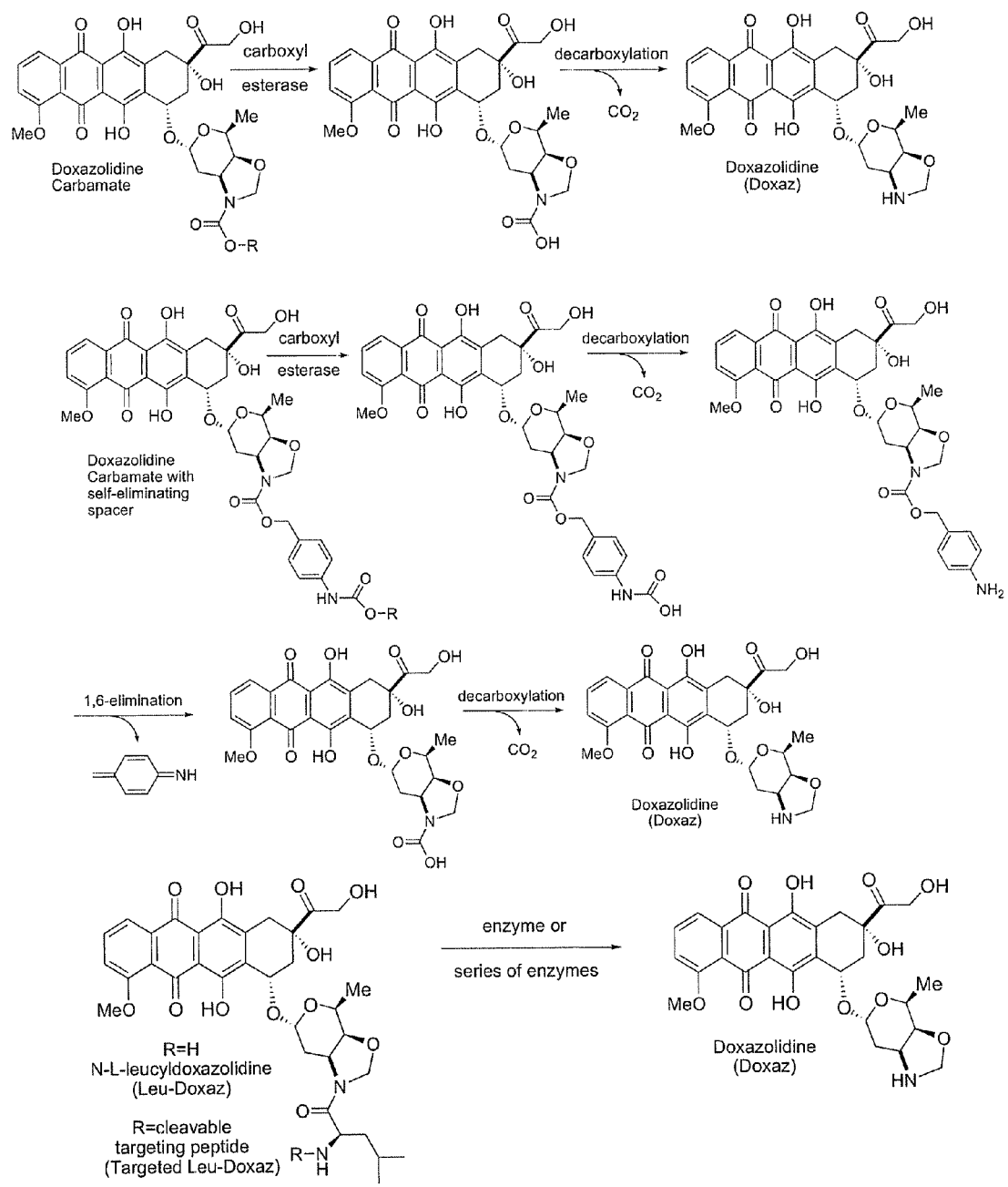
FIG. 6 shows a scheme for the enzymatic release of Doxazolidine from Doxazolidine carbamates and Doxazolidine carbamates with self-eliminating spacers. This figure also shows the enzymatic release of Doxazolidine from N-L-leucyldoxazolidine.

Formula I wherein R may be an alkyl group having between 1 and 100 carbon atoms, and preferably having between 4 and 6 carbon atoms. R may also be a cycloaklyl group having between 3 and 20 carbon atoms, such as a cyclohexyl or cyclopentyl alkyl group. R may also be an aryl group, and preferably a phenolic group such as phenyl, substituted phenyl, naphthyl or substituted naphthyl. In particularly preferred embodiments of the invention, R is butyl or pentyl. The synthesis and efficacy of these carbamates are described in Example 2 of this disclosure and the elimination of the ester alkyl group by carboxylesterases is depicted in FIG. 6.

Therefore, one embodiment of the present invention is a doxazolidine carbamate prodrug of doxazolidine that is enzymatically-activated by carboxylesterases. Preferably, the ester comprises an optionally-substituted alkyl group having between 1 and 100 carbon atoms, an optionally-substituted cycloaklyl group having between 3 and 20 carbon atoms, or an optionally-substituted aryl group and more preferably contains an unsubstituted alkyl group having between 4 and 6 carbon atoms or a phenyl or naphthyl group. Preferably, the doxazolidine prodrug of this embodiment has the chemical structure of Formula I.

2. Doxazolidine Carbamate Prodrugs Having a Self-Eliminating Spacer

Another useful doxazolidine prodrug of the present invention is a dual carbamate of doxazolidine in which a terminal carbamate is linked to doxazolidine through a p-aminobenzyloxycarbonyl (PABC) self-eliminating spacer. Therefore, one embodiment of the present invention is a compound having the chemical structure of Formula II:

Formula II

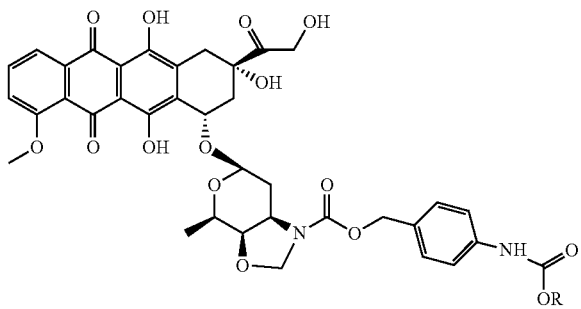

wherein R may be an alkyl group having between 1 and 100 carbon atoms and preferably having between 4 and 6 carbon atoms. R may also be a cycloaklyl group having between 3 and 20 carbon atoms, such as a cyclohexyl or cyclopentyl alkyl group. R may also be an aryl group, and preferably a phenolic group such as phenyl, substituted phenyl, naphthyl or substituted naphthyl. In particularly preferred embodiments of the invention, R is butyl (butyl PABC-Doxaz) or pentyl [Pentyl 4-(N-doxazolidinylcarbonyloxymethyl)phenylcarbamate; pentyl PABC-Doxaz]. These compounds having the p-aminobenzyloxycarbonyl (PABC) self-eliminating spacer show better growth inhibition while exhibiting reduced toxicity toward rat cardiomyocytes, relative to the parent drug doxorubicin. The synthesis and efficacy of these carbamate prodrugs are described in Example 2 of this disclosure and depicted in FIG. 7.

In these prodrugs, the terminal carbamate is selectively hydrolyzed to carbamic acid by endogenous carboxylesterases. A series of non-enzymatic steps including decarboxylation followed by 1,6-elimination and a second decarboxylation releases Doxazolidine. This activation by endogenous esterases followed by non-enzymatic decarboxylation and elimination steps is shown in FIG. 6.

Therefore, another embodiment of the present invention is a doxazolidine prodrug having two carbamate groups that is enzymatically-activated by carboxylesterases. Preferably, the terminal carbamate ester comprises an optionally-substituted alkyl group having between 1 and 100 carbon atoms or an optionally-substituted aryl group and more preferably contains an unsubstituted alkyl group having between 4 and 6 carbon atoms or a phenyl or naphthyl group. Preferably, the doxazolidine prodrug of this embodiment has the chemical structure of Formula II.

3. N-L-leucyl Carboxamide Derivatives of Doxazolidine

Another useful doxazolidine prodrug of the present invention is a leucyl carboxamide derivative of doxazolidine having the chemical structure of Formula III:

Formula III

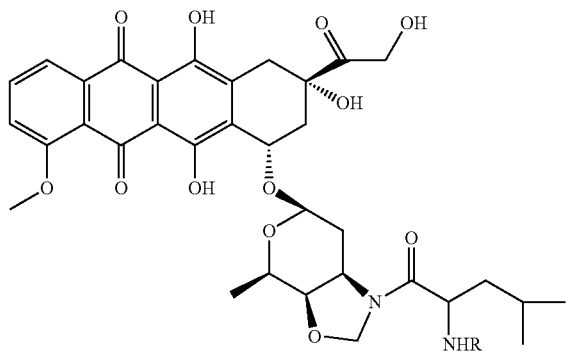

Wherein R is a biomolecule that is specifically removed by an enzyme present in a cancer cell. Preferably, R is a peptide that is cleaved by an enzyme other than leucine aminopeptidase or a carboxylesterase. Preferred R groups include D-Ala-Phe-Lys and glutaryl-Hyp-Ala-Ser-Chg-Gln-Ser [SEQ ID NO:1]. (Hyp is the abbreviation for a hydroxyproline residue and Chg for a cyclohexylglycine residue.)

Enzymatic cleavage at the amide bond by leucine aminopeptidase or carboxylesterase releases Doxazolidine from these prodrugs. The amino terminus of the leucine can be further conjugated to a peptide or other group cleaved by another enzyme to achieve a higher specificity of targeting. Preferably, the doxazolidine prodrug of this embodiment has the chemical structure of Formula III, wherein R may be glutaryl-Hyp-Ala-Ser-Chg-Gln-Ser [SEQ ID NO: 1], cleaved by prostate specific antigen (PSA) between the Ser and Leu residues, and D-Ala-Phe-Lys, cleaved by plasmin between Lys and Leu.

4. Doxazolidine Prodrugs Activated by Plasmin.

The oxazolidine ring of Doxaz is hydrolytically sensitive, especially at low pH. However, it has been shown that the oxazolidine ring of a series of oxazolidine carbamates was stable above pH 7 for days, but could be hydrolyzed within 24 hours under acidic conditions (Rona, M. and Ben-Ishai, D., J. Org. Chem., 26: 1446-1450 (1961)). Similarly, the ethyl carbamate of Doxaz exhibits excellent stability and can be purified by silica gel chromatography or HPLC. This discovery has led to the development and synthesis of plasmin-activated prodrugs of Doxaz in which the final amine deprotection can be carried out under mild reaction conditions after formation of the peptide/Doxaz carbamate. These prodrugs incorporate the active anti-cancer drug Doxaz with the oxazolidine ring protected as a carbamate having a spacer between the oxazolidine ring and a peptide incorporating a plasmin cleavage site. Preferably the spacer between the oxazolidine ring and the peptide is one or two para-aminobenzyloxycarbonyl (PABC) spacers. Following cleavage of the peptide by plasmin, the self-eliminating PABC spacer is exposed and separates, releasing the active Doxaz anti-cancer compound.

Plasmin is a serine protease produced by cleavage of plasminogen at the tumor cell surface predominantly by urokinase plasminogen activator (uPA) bound to its receptor urokinase plasminogen activator receptor (uPAR). Activation of plasminogen to plasmin on the surface of pancreatic cancer cells by tissue plasminogen activator (tPA) bound to annexin II has also been observed. Plasminogen is present in blood plasma at approximately 2 μM concentration and is also present in extravascular compartments. Plasmin catalyzes the breakdown of proximal extracellular matrix proteins, but not distal proteins, because of a short half-life in circulating blood from the serpin, α2-antiplasmin and α2-macroglobulin protease inhibitors. Therefore, these Doxaz prodrugs that have a stabilized oxazolidine ring and a peptide having a plasmin cleavage site are inactive and non-toxic in the bloodstream, but are activated to greater extent near cancer cells that activate the plasmin enzyme. Thus, one embodiment of the present invention is a prodrug of Doxaz having the chemical structure of Formula IV:

Formula IV

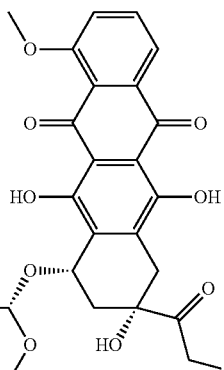
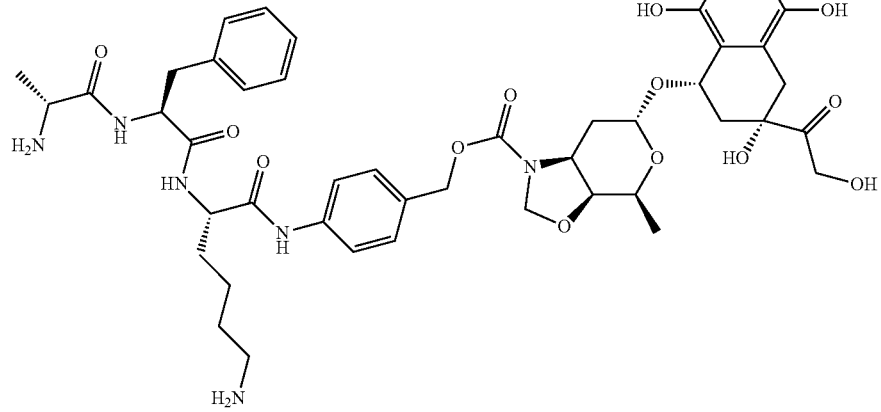

or a pharmaceutically-acceptable salt thereof.

This prodrug of Doxaz, D-Ala-L-Phe-L-Lys-p-aminobenzyloxycarbonyl-Doxaz (aFK-PABC-Doxaz), has a plasmin-cleavable peptide and the self-eliminating PABC spacer, which is selectively cleaved by plasmin to release Doxaz, to inhibit the growth of both sensitive and resistant cancer cells at low concentration. It will also inhibit the growth of normal endothelial cells recruited for tumor angiogenesis that also express plasmin. Further, Doxaz that escapes the site of release from aFK-PABC-Doxaz will rapidly hydrolyze to the less cytotoxic Doxorubicin.

This Doxaz prodrug is formed by coupling Doxazolidine to alloc-D-Ala-L-Phe-L-(alloc)Lys-p-aminobenzyl alcohol via activation of its alcohol with p-nitrophenyl chloroformate followed by deprotection with palladium zero. aFK-PABC-Doxaz is a good substrate for plasmin with a half-life of about 6 minutes in the presence of plasmin at 37° C., and Doxaz is observed as an intermediate between aFK-PABC-Doxaz and Doxorubicin during the hydrolysis.

A closely related embodiment of the present invention is another prodrug of Doxaz having two PABC spacers linking the Doxaz active anti-tumor compound and a plasmin cleavage site. This embodiment of the present invention has the chemical structure of Formula V:

Formula V

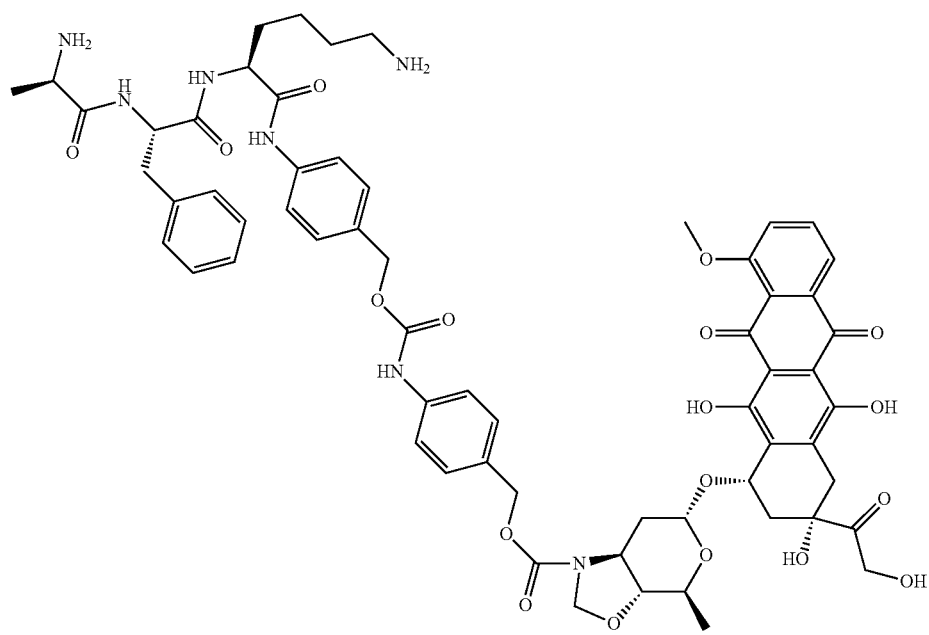

or a pharmaceutically-acceptable salt thereof.

The activity, limited toxicity and synthesis of these plasmin-activated prodrugs of Doxaz are described in Example 3 of this disclosure. As noted in Example 3, the plasmin protease inhibitors prevalent in the bloodstream prevent the plasmin-mediated cleavage of a plasmin cleavage site, such as Lys-Phe-D-Ala, from these prodrugs, thereby eliminating or significantly reducing the cardiotoxic side effects of Doxaz when these prodrugs are used in vivo. Despite their limited cardiotoxicity, these plasmin-activated carbamate derivatives of Doxaz having the chemical structures depicted in Formulas IV and V exhibit superior cancer cell growth inhibition and are therefore useful for treating or inhibiting the growth of cancer in mammals. These results indicate that these plasmin-activated prodrugs posses many of the desired characteristics of a functional prodrug of an anti-cancer compound. For example, the stability of these drugs in buffer and serum for over 6 hours shows the improved stability of the oxazolidine ring of Doxaz conferred by the derivatization as a carbamate, and the compounds exhibit excellent water solubility as a di-cation. Additionally, these drugs show specific, rapid and efficient conversion of the prodrug to Doxaz by the enzyme of choice without the use of additional cofactors as plasmin incubation results in approximately 50% conversion to Doxaz within about 8 minutes. Also, these prodrugs release an active compound that has good diffusivity for an optimal bystander effect as Doxaz is more lipophilic than Doxorubicin and diffuses into cancer cells much more rapidly than Doxorubicin. Further, these prodrugs exhibit reduced cardiotoxicity relative to the active compound as the two prodrugs are about fifty-fold less toxic to rat cardiomyocytes than Doxorubicin. Finally, the active drug released by these prodrugs has a short half-life after tumor-localized activation, thereby reducing its spread to normal tissue because, after prodrug activation near a tumor, Doxaz will have a short half-life of about 3 minutes.

5. Doxazolidine Prodrugs Activated by β-Glucuronidase.

Because the glycosidic enzyme β-glucuronidase is largely confined to lysosomes, the serum levels of the endogenous enzyme are extremely low and therefore, prodrugs of Doxaz stabilized by a glucuronide moiety that can be removed by β-glucuronidase, thereby releasing the active anti-cancer moiety, will have limited systemic release and thus, limited disseminated toxicity. These prodrugs can be selectively activated in tumors by human β-glucuronidase. Thus, one embodiment of the present invention is a Doxaz prodrug composed of Doxaz conjugated to glucuronide through at least one PABC spacer (Doxaz-PABC-Glucuronide). As determined for the kinetic and in vitro data for Doxaz-PABC-Lys-Phe-D-Ala prodrugs (described supra), the PABC spacer is very effective in the enzymatic conversion of prodrug to Doxaz and therefore, this spacer is incorporated into the glucuronide prodrug shown in FIG. 10. Upon enzymatic cleavage by β-glucuronidase, a 1,6-elimination will quickly release the parent anthracycline (Doxaz) from the iminoquinone methide protecting group. This Doxaz-PABC-Glucuronide prodrug conjugate has the chemical structure of Formula VI:

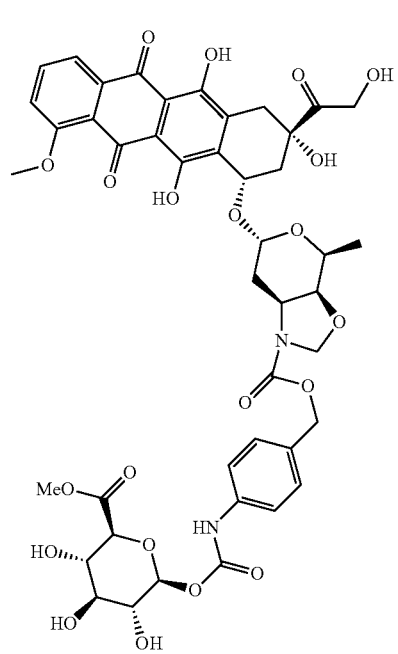

Formula VI or a pharmaceutically-acceptable salt thereof.

The synthesis of these Doxaz-glucuronide prodrug conjugates is described in Example 4 of this disclosure. Because Doxaz is, on average, about 100-fold more cytotoxic than Doxorubicin against numerous sensitive cancer cell lines and because Doxaz rapidly converts to Doxorubicin in vivo (with a half-life of about 3 minutes), Doxaz is highly cytotoxic for only a short time, which is ideal for tumor-localized prodrug activation. In addition, since Doxaz is more lipophilic than Doxorubicin (calculated LogP=1.1 vs. 0.34), the potential bystander effect of this prodrug following activation by β-glucuronidase is much greater.

6. Doxazolidine Prodrugs Activated by Carboxypeptidase G2.

The most effective Doxorubicin prodrugs incorporate a peptide or sugar recognized and cleaved by endogenous or non-native-enzymes near the tumor or its supporting vasculature to reduce the dose-limiting cardiotoxic side effect of Doxorubicin. Most of these Doxorubicin prodrugs show significantly lower cardiotoxicity while maintaining the anti-tumor activity of Doxorubicin in mouse tumor models. Using this strategy, the present inventors have devised prodrugs of Doxazolidine activated in vivo by non-native enzymes delivered to the tumor site separately from the prodrug itself. The enzymes are delivered to the cancer cells through the ADEPT or PeDEPT strategies described above in which the enzymes that specifically activate the Doxaz prodrug are delivered to the cancer cells by an antibody, an antibody fragment, or small peptides that bind specifically and with high affinity to a cell surface protein that is only expressed (or is over-expressed) in cancer cells.

As noted above, ADEPT and GDEPT generally suffer from the large size and immunogenic response-inducing characteristics of the antibodies or antibody fragments. Peptides containing Arg-Gly-Asp (RGD), however, have been used to deliver a number of molecules to tumor cells and associated angiogenesis including radioisotopes, drugs, proteins, antibodies, liposomes, plasmids, vectors, and viruses. Although some RGD-containing peptides bind to numerous integrins, the peptide Lys-Arg-Gly-Asp-phe (KRGDf) [SEQ ID NO:2] binds $\alpha_v\beta_3$ with excellent specificity. RGD peptides function most effectively as targeting peptides when they are cyclic. In a preferred embodiment of the present invention the KRGDf targeting peptide is a cyclic peptide, wherein K is bonded to f via an amide functional group using its α-amino group. This allows the ε-amino of K to be free for attachment to the enzyme.

The present inventors use the novel strategy of employing an RGD-containing peptide to deliver an enzyme to a tumor for the activation of a prodrug. This peptide-directed enzyme prodrug therapy (PeDEPT) utilizes the high binding affinity and $\alpha_v\beta_3$ integrin specificity (1000-fold better for $\alpha_v\beta_3$ than for $\alpha_{IIb}\beta_3$ platelet receptor) of KRGDf to localize prodrug-activating enzymes to tumors. The primary advantage of PeDEPT is the small size of the peptide KRGDf (M.W. approx. 600), resulting in a smaller peptide-enzyme conjugate with superior pharmacokinetics and enzymatic efficiency relative to an antibody-enzyme construct. Numerous studies have verified that a multivalent RGD peptide interaction with $\alpha_v/\beta_3$ integrin can result in significant endocytosis of the peptide/macromolecule construct. Therefore, attachment of several KRGDf peptides per enzyme molecule triggers internalization of the prodrug-activating conjugate and decreases the chances for successful PeDEPT by reducing the bystander effect. However, the super-activated state of $\alpha_v\beta_3$, which binds RGD peptides with very high affinity, cannot transduce the proper signals needed for internalization. Additionally, a single RGD fragment contained in a 30 kDa fusion protein (CBD-RGD) is sufficient to create good binding affinity to $\alpha_v\beta_3$-overexpressing cells. By conjugating one to four molecules of KRGDf per enzyme molecule, good binding affinity/selectivity can be achieved without the risk of substantial peptide/enzyme conjugate internalization. Therefore, one embodiment of the present invention is a method of activating a prodrug at the surface of a cell by the separate administration of an enzyme that will specifically activate the prodrug, linked to a peptide that binds to a protein on or in the target cells with great affinity. Using this PeDEPT approach, the enzyme linked to the peptide is administered prior to the administration of the prodrug activated by that enzyme. Preferably, the target cells are cancer cells and the peptide is a RGD peptide or an RGD peptide fragment that binds to $\alpha_v\beta_3$ integrin with high affinity. More preferably, the peptide is KRGDf. Most preferably, the peptide is KRGDf that is linked to the activating enzyme in a ratio of KRGDf peptide:activating enzyme of between about 1:1 to about 4:1. In one embodiment of the present invention, the enzyme is carboxypeptidase G2.

The immunogenicity of non-native enzymes may be reduced by PEGylation. Introduction of a Cys residue in engineered proteins provides a free thiol for in site-specific PEGylation. This method of reducing immunogenicity does have disadvantages however, such as low yield of PEGylated protein and significant loss of enzymatic activity caused by the introduction of the Cys residue. Therefore, this method can optionally be incorporated into the methods of delivering a prodrug-activating enzyme to a target site of the present invention if the activating enzyme-peptide conjugate is found to illicit an immunogenic reaction in the host.

Figure 10:
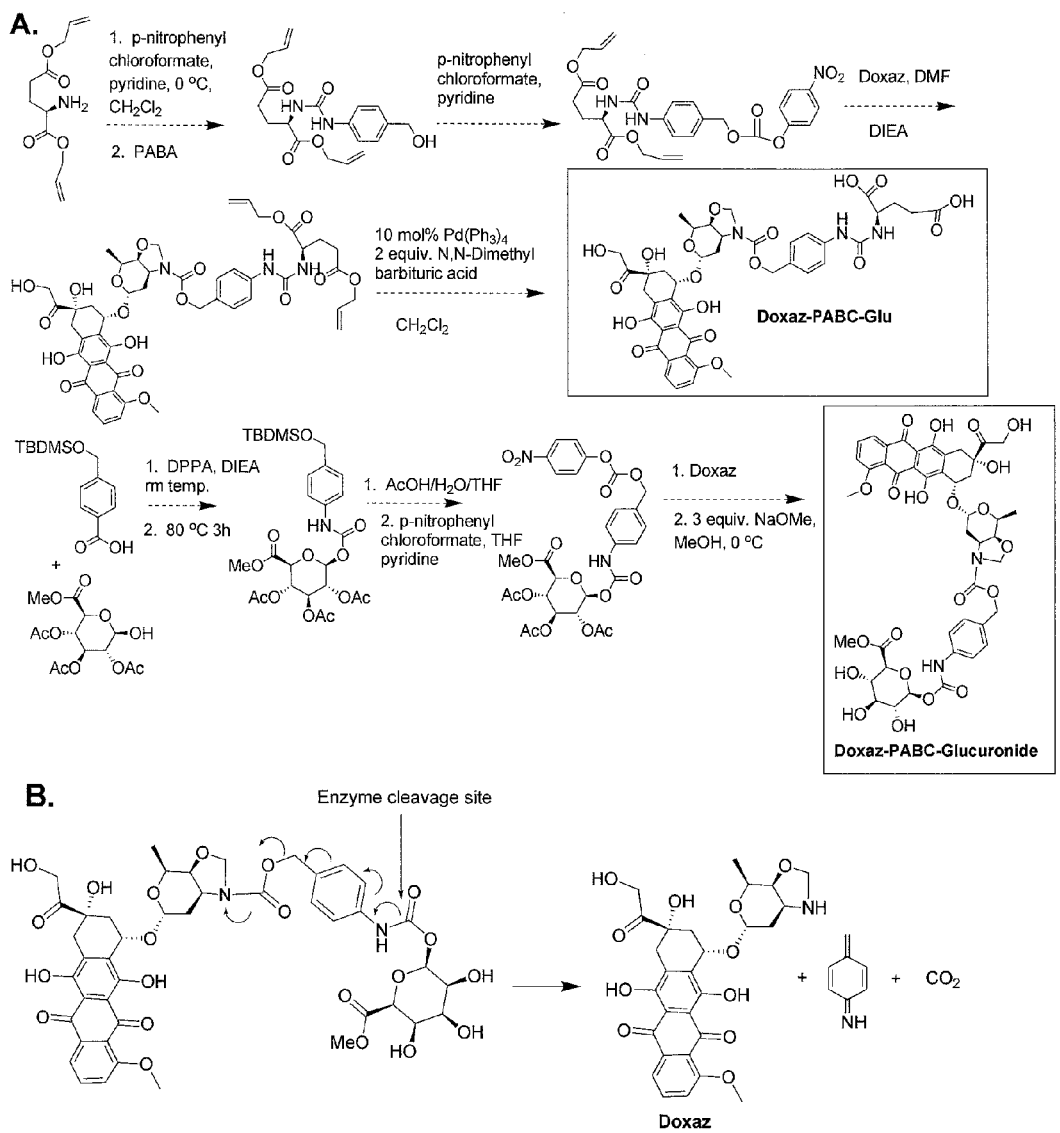
FIG. 10A shows synthesis schemes for Doxaz prodrugs activated by carboxypeptidase G2 (Doxaz-PABC-Glu) and β-glucuronidase (Doxaz-PABC-Glucuronide) in which carboxylic acids are protected as allyl esters to accommodate mild deprotection conditions for the final product. Abbreviations used in these synthesis schemes: PABA, p-aminobenzyl alcohol; DIEA, di-isopropylethylamine, DPPA, diphenylphosphorylazide; TBDMS-, t-butyldimethylsilyl-.
FIG. 10B shows mechanisms for enzyme cleavage and release of the active anti-cancer Doxaz drug from these prodrugs via a 1,6-elimination.

Thus, another embodiment of the present invention is a Doxaz prodrug that is activated by the enzyme carboxypeptidase G2 that is present at the surface of cancer cells by the prior administration of a tumor-specific monoclonal antibody or peptide conjugated to the carboxypeptidase enzyme. This prodrug (Doxaz-COBAC-Glu) contains Doxazolidine conjugated to glutamic acid through at least one PABC spacer, as shown in FIG. 10. Upon enzymatic cleavage by carboxypeptidase G2, a 1,6-elimination quickly releases the parent anthracycline (Doxaz) from the iminoquinone methide protecting group. The carboxypeptidase G2-activated prodrug of the present invention has the chemical structure of Formula VII:

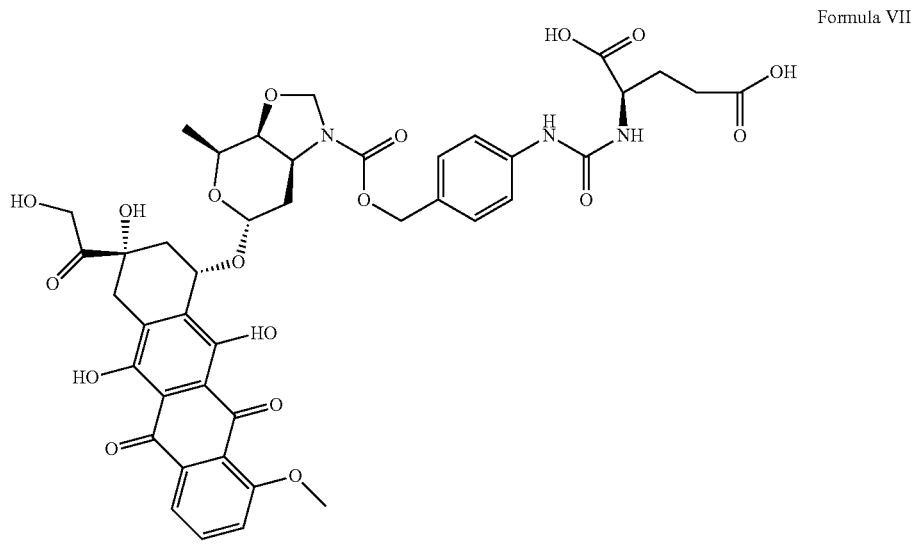 [SMILES: COc1cccc2c1C(=O)c1c(O)c3c(c(O)c1C2=O)C[C@@](O)(C(=O)CO)C[C@@H]3O[C@H]1C[C@H]2[C@H](OCN2C(=O)OCc2ccc(NC(=O)N[C@H](CCC(=O)O)C(=O)O)cc2)[C@H](C)O1]

Formula VII or a pharmaceutically-acceptable salt thereof.

Site-specific activation of this prodrug requires the presence of carboxypeptidase G2 at the surface of the cancer cell(s). As noted above, the presence of this non-native activating enzyme is achieved by the prior administration of a tumor-specific monoclonal antibody or peptide conjugated to carboxypeptidase G2. Preferably, the time between administration of the enzyme conjugated to the targeting antibody or peptide and this prodrug is about 7 hours. Further, while a physician will determine the dosage of the enzyme used, the dose of enzyme is preferably about 1000 units/kg. The synthesis of this prodrug is described in Example 5 of this disclosure.

7. Doxazolidine Prodrugs Activated by β-Lactamase.

As described above, a novel drug delivery strategy of the instant invention is the administration of a prodrug that is specifically activated to the active drug by a non-native enzyme that is present at the target site of activation following the administration of that activating enzyme conjugated to a targeting peptide. The targeting peptide is chosen for its ability to bind to a protein present at the target site, such as a protein expressed on the surface of a cancer cell, and to successfully deliver activating enzyme to the target site. For the reasons explained above, the target cells are preferably cancer cells and the peptide is preferably a RGD peptide or a RGD-peptide fragment that binds to $\alpha_v\beta_3$ integrin with high affinity. More preferably, the peptide is KRGDf. Most preferably, the peptide is KRGDf that is linked to the activating enzyme in a ratio of KRGDf peptide:activating enzyme of between about 1:1 to about 4:1. In this embodiment of the invention, the enzyme is β-lactamase.

Therefore, the present inventors have also designed a Doxaz prodrug that is activated by the enzyme β-lactamase that is present at the surface of cancer cells by the prior administration of a tumor-specific monoclonal antibody or peptide conjugated to the β-lactamase enzyme. This prodrug (Doxaz-Cephem) contains a carbamate of Doxazolidine conjugated to cephalosporanic acid. This β-lactamase-activated prodrug of the present invention has the chemical structure of Formula VIII:

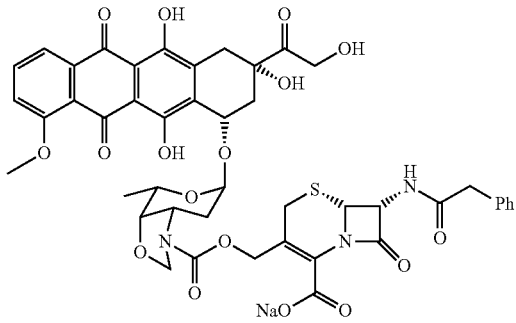

or a pharmaceutically-acceptable salt thereof

Site-specific activation of this prodrug requires the presence of β-lactamase at the surface of the cancer cell(s). The presence of this non-native activating enzyme is achieved by the prior administration of a tumor-specific monoclonal antibody or peptide conjugated to β-lactamase. Preferably, the time between administration of the enzyme conjugated to the targeting antibody or peptide and this prodrug is about 7 hours. Further, while a physician will determine the dosage of the enzyme used, the dose of enzyme is preferably about 1000 units/kg. The synthesis of this prodrug is described in Example 6 of this disclosure, C. Pharmaceutical Compositions The anti-cancer compounds of the present invention may possess a center of chirality and can exist as optical isomers. Both the racemates of these isomers and the individual isomers themselves, as well as diastereomers when there are two chiral centers, are within the scope of the present invention. The racemates can be used as such or can be separated into their individual isomers mechanically as by chromatography using a chiral adsorbent. Alternatively, the individual isomers can be prepared in chiral form or separated chemically from a mixture so as to obtain either or both substantially free of the other; i.e., in a form having an optical purity of >95%.

The present invention also pertains to the pharmaceutically-acceptable non-toxic acid addition salts of the anti-cancer doxazolidine compounds. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The compositions are preferably formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an irradiate, sustained or delayed release of active ingredient after administration to the patient by employing procedures well known in the art.

Oral dosage forms include tablets, capsules, dragees, and similar shaped, compressed pharmaceutical forms containing from about 1 mg to about 100 mg of drug per unit dosage. Isotonic saline or dextrose solutions containing from about 20 mg/mL to about 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of the present invention associated with at least one pharmaceutically acceptable carrier, diluent or excipient. In preparing such compositions, the active ingredients are usually mixed with, or diluted by, an excipient or enclosed within such a carrier, which can be in the form of a capsule or sachet. When the excipient serves as a diluent, it may be a solid, semi-solid, or liquid material that acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, polysorbate, Cremophore ELP, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The active doxazolidine compounds are effective over a wide dosage range and are generally administered in a pharmaceutically effective amount. It will be understood, however, that the amount of the compounds actually administered will be determined by a physician, in the light of the relevant circumstances, including the condition to be treated, the chosen route of administration, the actual compound administered, the age, weight, and response of the individual patient, the severity of the patient's symptoms, and the like.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks, or intermittent positive pressure breathing machine. Solution, suspension, or powder compositions may be administered, preferably orally or nasally, from devices that deliver the formulation in an appropriate manner.

Additional objects, advantages, and novel features of this invention will become apparent to those skilled in the art upon examination of the following examples thereof, which are not intended to be limiting.

EXAMPLES

Example 1

Doxazolidine (Doxaz)

Synthesis and Characterization of Anti-Cancer Activity

Analytical HPLC injections were onto an Agilent Zorbax 5 μm reverse-phase octadecylsilyl (ODS) microbore column, 4.6 mm i.d.×150 mm, eluting at 1.0 mL/min, and the eluent was monitored at 280 and 480 nm. Analytical separation was achieved using method #1 parameters: flow rate, 1.0 mL/min; eluents A=HPLC grade acetonitrile and B=20 mM triethylammonium acetate, pH 7.4; gradient, 25:75 A/B at 0 min to 70:30 A/B at 10 min, isocratic to 11 min, back to 25:75 A/B at 13 min. HPLC method #2 parameters were used for monitoring hydrolysis of drugs: flow rate, 1.0 mL/min; eluents A=HPLC grade acetonitrile and B=20 mM triethylammonium acetate, pH 7.4; gradient, 25:75 A/B at 0 min to 56:44 A/B at 7 min, isocratic to 7.5 min, back to 25:75 A/B at 8.5 min, isocratic to 9 min. Electrospray mass spectra were measured with a Perkin-Elmer Sciex API III instrument (Norwalk, Conn.), equipped with an ion-spray source, at atmospheric pressure.

Synthesis of Doxorubicin oxazolidine, Doxazolidine (Doxaz). The original syntheses of DoxF and its congeners, Daunoform and Epidoxoform (EpiF), were all performed by reaction of the respective clinical drug as its hydrochloride salt with formalin, an aqueous methanolic solution of formaldehyde, in acetate buffer at pH 6. The dimeric conjugates were extracted into chloroform as they were formed.

Doxorubicin hydrochloride (40 mg, 69 μmol) formulated with lactose (clinical sample) was dissolved in 100 mL, of saturated sodium carbonate/sodium bicarbonate buffer, pH 8.5. The aqueous solution was then extracted three times with 250 mL of chloroform. The chloroform extracts were combined, dried over sodium sulfate, filtered, and the chloroform was removed by rotary evaporation yielding doxorubicin as the free base. Doxorubicin free base (30 mg, 55 μmol) was dissolved in 17 mL of deuteriochloroform (3.7 mM) that had been dried over 4 Å molecular sieves for at least 24 h, and the solution was degassed with argon. To this solution, 10 mg of paraformaldehyde (30% by weight of doxorubicin) was added and the solution was allowed to stir in the dark at ambient temperature (25 to 28° C.). Progress of the reaction was followed by $^1$H NMR and additional paraformaldehyde (10 mg) was added at 2 and 4 days if further progress was not observed. After 7 days, the reaction was complete as determined by observation of appearance of oxazolidine doublets at 4.31 ppm and 4.68 ppm and shift of the peak for the 5'-methyl from 1.36 ppm to 1.34 ppm. The reaction mixture was filtered to remove excess paraformaldehyde and solvent removed by rotary evaporation to dryness followed by evacuation (approx. 0.05 Torr) for 30 min to give 22 mg of Doxaz (40 mmol, 73% from doxorubicin free base) isolated as a red film. Product was characterized and analyzed for purity by 500 MHz $^1$H NMR in chloroform-d (>90% pure). Positive ion electrospray mass spectrometry of a solution in THF showed a doubly-charged ion at m/z 278.8 ((M+2H$^+$)/2, 100% rel. intensity, calc 278.8). HPLC shows a peak for Doxaz at 6.6 min (Doxorubicin elutes at 4.7 min); HPLC was not reliable for product purity because of some hydrolysis to Doxorubicin during elution.

In contrast, reaction of Doxorubicin free-base in chloroform-d solvent with larger amounts of paraformaldehyde, the polymer of formaldehyde, with monitoring by $^1$H NMR, showed formation of Doxaz followed by formation of DoxF. Doxaz was isolated 90% pure (73% yield) by stopping the reaction at an intermediate time with the only impurities being traces of Doxorubicin and DoxF. Correspondingly, DoxF was isolated in greater than 90% purity (79% yield) by allowing the reaction to continue, again with the only impurity being Doxaz. The structure of Doxaz was established from an intense, doubly-charged molecular ion at m/z 278.8 in the electrospray mass spectrum and from the high resolution $^1$H NMR data with all of the J-couplings assigned in comparison with data for DoxF. Of particular note in the NMR spectrum of Doxaz is the absence of the singlet peak for the methylene connecting the two oxazolidine rings of DoxF and the characteristic small geminal coupling constant for the methylene protons of the oxazolidine.

The NMR data also partially establish the conformation of the daunosamine sugar of Doxaz and DoxF in chloroform solution as a chair. The proton at the 1'-position is coupled approximately equally to the two protons at the 2'-position in both structures indicating similar dihedral angles and a chair conformation. Although this is consistent with what others have observed in the crystal structures of various anthracycline antitumor drugs and in the crystal structures of Daunorubicin (FIG. 1) and Epidoxorubicin cross-linking DNA, it is not consistent with what is now observed in the crystal structure of DoxF.

Crystal structure of DoxF. X-ray quality crystals were grown at the interface of a chloroform solution of DoxF and a mixture of ethyl acetate mixed with hexane. Crystallization of the DoxF was accomplished by placing 10 mg of the crude material inside a 4 mm i.d. glass tube and dissolving it in 0.5 mL of chloroform. The crystal was centered in the beam (Mo-Kα; λ=0.71073 Å; graphite monochromator). A preliminary orientation matrix and unit cell constants were determined by the collection of 60 10-s frames, followed by spot integration and least-squares refinement. A sphere of data were collected at −119° C. using 0.3° ω scans. Absorption correction was applied using SADABS. The data were corrected for Lorentz and polarization effects, but no correction for crystal decay was applied. Structure solutions and refinements were performed (SHELXTL-Plus V5.0) on F-squared. The data are indicative of a primitive trigonal cell. Systematic absences and intensity statistics suggested space groups $P3_1$ (#144) and $P3_2$ (#145). Acceptable solution and refinement in space group $P3_1$ was achieved with stereochemistry consistent with that known for DoxF. Since DoxF is a weak anomalous scatterer, the Flack parameter was poorly defined, but it is near zero (−0.24(18)). The inverted structure gave unsatisfactory refinement in $P3_1$ and a Flack parameter approaching unity. All non-H atoms in the model were refined anisotropically. Hydrogens were placed in idealized positions and were included in structure factor calculations but were not refined.

The crystal structure shows a compact structure with the daunosamine sugars in a twist boat conformation and the anthraquinone rings in a π-stacking arrangement. The crystal structure shows an assortment of intramolecular and four notable intermolecular hydrogen bonds. Loss in stability from the twist boat sugar conformations in the solid state with little or no anomeric effect is clearly compensated, partially through π-stacking but probably more importantly through favorable intermolecular interactions including hydrogen bonds.

In vitro Activity. $IC_{50}$ measurements were performed by dissociating cells with trypsin/EDTA, counting and suspending the cells in growth media to a concentration of $5\times10^3$ cells/mL. This cell suspension was dispensed in 200 µL aliquots (1000 cells/well) into the inside wells of 96-well tissue culture plates. Outside wells contained 200 µL of media. Plates were then incubated for 24 h at 37° C. in a humidified atmosphere of 5% CO, and 95% air. The medium was replaced with 90 µL of growth medium prior to addition of the drug. Doxaz was dissolved in DMSO at concentrations ranging from 50 µM to 1 mM. The concentration was then corrected by measuring the solution absorbance at 480 nm ($\epsilon$=11,500 M$^{-1}$ cm$^{-1}$). Serial dilutions (1:3 and 1:10) were made in sterile DMSO to yield seven solutions of decreasing drug concentration at 100× the respective working concentrations. The resulting solutions were individually diluted 1:10 in RPMI 1640 medium; 10 µL of the resulting 10× solution was immediately added to the appropriate lane of cells. Additionally, two lanes were treated with 10 µL of growth medium containing 10% sterile DMSO and one lane was treated with 90 µL of 1.5 M Tris HCl. The cells were incubated at 37° C. for 3 h, at which time the drug solutions were replaced with 200 µL of fresh growth medium. The cells were then incubated for 5 days and the extent of colony formation was determined using a crystal violet staining assay measuring optical density at 588 and 770 nm.

Drug uptake was measured by flow cytometery. Cells were dissociated with trypsin/EDTA, counted, and suspended in growth media to a concentration of $1\times10^5$ cells/mL. This cell suspension was dispensed in 2.5 mL aliquots into 6-well tissue culture plates. Plates were then incubated for 24 h at 37° C. in a humidified atmosphere of 5% $CO_2$ and 95% air. The growth media was replaced with 2 mL of fresh growth media prior to addition of the drug. Doxaz, DoxF, and Doxorubicin HCl were dissolved in DMSO each at a concentration of 50 µM. The concentration was then corrected by measuring the solution absorbance at 480 nm ($\epsilon$=11,500 M$^{-1}$ cm$^{-1}$). Drug solution (20 µL) was added to an individual well and was incubated for 5 min, 15 min, 30 min, 1 h, 2 h or 3 h at 37° C. in a humidified atmosphere of 5% $CO_2$ and 95% air. All drug treatments were performed so all treatment times would end simultaneously. After treatment, culture media was removed, cells washed once with 0.5 mL HBSS, washed once with 0.5 mL trypsin/EDTA, and 0.5 mL trypsin/EDTA was added and cells were incubated for 5 min. After all cells were trypsinized, cells were aspirated with 1.5 mL cold D-PBS (Dulbecco's phosphate buffered saline, no calcium or magnesium) and this solution was added to 3 mL of cold D-PBS (4.5 mL total D-PBS) in a conical vial. Cells were centrifuged at 200 g for 5 min, and D-PBS was decanted off. Cells were washed once more in 5 mL cold D-PBS, centrifuged at 200 g for 5 min and D-PBS was decanted off. The cells were then aspirated with 1 mL D-PBS, placed in a sample tube, and kept on ice until needed with FACScan. Cells were analyzed with excitation at 488 nm (15 mW Ar ion laser), with emission monitored between 570 nm and 600 nm. Instrument settings were optimized for the cell line and held constant for all experiments; for the anthracycline fluorescence analysis, 10,000 cells were analyzed for each sample. The data are presented as the mean fluorescence for each condition.

Hydrolysis of Doxaz or DoxF in RPMI medium was performed by dissociating the cells with trypsin/EDTA, counting and then suspending the cells in growth media to a concentration of $5\times10^3$ cells/mL. This cell suspension was dispensed in 200 µL aliquots (1000 cells/well) into the inside wells of 96-well tissue culture plates. Plates were then incubated for 24 h at 37° C. in a humidified atmosphere of 5% CO, and 95% air. The medium was replaced with 180 µL of growth medium prior to addition of the drug. RPMI media (no serum added) was divided into 5 mL aliquots in conical vials and heated to 37° C. in a constant temperature bath. Doxaz and DoxF were dissolved in DMSO at a concentration of 1 mM equivalents. The concentration was then corrected by measuring the solution absorbance at 480 nm ($\epsilon$=11,500 M$^{-1}$ cm$^{-1}$). Drug solution (50 µl) was added to an individual conical vial and the drug was allowed to hydrolyze (at 10 µM) for 0, 10, 20, 30, 45, 60, 75 or 90 min. Experiments were performed such that all hydrolysis times would end simultaneously. After hydrolysis, 20 µL of the drug solution was added to a lane of wells on the 96-well plate to give a final concentration of 1 µM equivalents (sum of Doxorubicin, Doxaz and/or DoxF) for treatment of cells. Additionally, two lanes were treated with 20 µL of growth medium containing 1% sterile DMSO for a control. The cells were incubated at 37° C. for 3 h, at which time the drug solutions were replaced with 200 µL of fresh growth media. The cells were then incubated for 5 days, and the extent of colony formation was determined using a crystal violet staining assay measuring optical density at 588 and 770 nm.

Hydrolysis of DoxF in RPMI medium or 100% human serum was performed as described above except drug hydrolysis was performed at 1 µM equivalents and drug treatment was at 100 nM equivalents. During drug treatment, the medium was either 90% RPMI/10% FBS or 90% RPMI/10% human serum. During cell growth, the medium was 90% RPMI/10% FBS.

The inhibition of growth of three breast and one prostate cancer cell lines by Doxorubicin, DoxSF, DoxF and Doxaz is compared in Table 1.

TABLE 1

Comparison of growth inhibition of breast and prostate cancer cells by Doxorubicin, DoxSF, DoxF, Doxaz, Epi and EpiF.

| Compound | $IC_{50}$ | | | |
|---|---|---|---|---|
| | MCF-7 | MCF-7/Adr | MDA-MB-435 | DU-145 |
| Doxorubicin | 200 ± 26 | 10,000 ± 1300 | 150 ± 14 | 240 |
| DoxSF | 70-80 | 800-2000 | 50 ± 9 | — |
| DoxF | 2 | 1 | — | 3 |
| Doxaz | 3 ± 0.2 | 3 ± 0.2 | 7 ± 0.3 | 4 ± 0.6 |
| Epi | 200 | >10,000 | — | 380 ± 52 |
| EpiF | 65 | 70 | — | 26 ± 5 |

Units for $IC_{50}$ values with Doxorubicin, DoxSF, Doxaz and Epi are nM and with DoxF and EpiF, nM equivalents to correct for DoxF and EpiF having two active compounds per molecule. All determinations of the $IC_{50}$ values for Doxaz were done at least in duplicate, with average data shown. Errors represent one standard deviation about the mean for the six wells per lane measured for each drug concentration.

These data show that DoxF and Doxaz inhibit 50% growth at approximately the same concentration for each cell line and inhibit growth at one to greater than three orders of magnitude lower concentration than Doxorubicin. The more dramatic difference occurs with the multidrug resistant MCF-7/Adr cells that overexpress P-170 glycoprotein efflux pump amongst other resistance mechanisms. The ability of Doxaz to inhibit the growth of MCF-7/Adr cells as well as DoxF is illustrated in FIG. 4A which shows cell growth as a function of drug treatment within a single experiment. All data points fall on the same growth inhibition curve. Growth inhibition parallels drug uptake as measured by flow cytometry measuring drug fluorescence as a function of time after drug treatment, MCF-7/Adr cells take up significantly more DoxF and Doxaz than Doxorubicin, as shown in FIG. 3B.

Hydrolytic Stability of DoxF and Doxaz.

Doxaz stability in DMSO. Doxaz (22 mg, 40 µmol) was dissolve in 1 mL of DMSO-$d_6$ (stored over activated 4 Å molecular sieves) and analyzed for purity by 500 MHz $^1$H NMR. After a 10× dilution with DMSO to a concentration of 4 mM, the stability of Doxaz was then followed by HPLC, observing the relative peak area of the Doxaz peak at 6.6 min with constant injection volume. Doxaz hydrolyzed at a rate of <2% per day in DMSO. Doxaz stability in buffers. HPLC buffer, pH 7.4, 20 mM TEAA, was used for the measurement of hydrolysis of Doxaz. The buffer's pH was adjusted as needed with either triethyl amine or acetic acid to pH 10.4, 9.0, 6.0 and 5.0 with one sample left unchanged at pH 7.4. A volume of 1950 µL of each of these solutions was added to a conical vial and then cooled to 14° C. 50 µL of a 4 mM solution of Doxaz was added to each tube and hydrolysis was followed by HPLC with injections every 10 min. The pH of the buffers was measured before the addition of drug and 1.5 h after the start of hydrolysis.

Both DoxF and Doxaz are relatively stable in dry chloroform and dry DMSO over a period of days. In dry DMSO, Doxaz hydrolyzes to Doxorubicin at less than 2% per day at ambient temperature. In aqueous medium, DoxF is very hydrolytically unstable with respect to formation of Doxaz, and Doxaz is hydrolytically unstable with respect to formation of Doxorubicin. Injection of DoxF on reverse phase HPLC only shows peaks for Doxaz and Doxorubicin. Consequently, HPLC was used to monitor the kinetics of hydrolysis of Doxaz to Doxorubicin at 14° C. as a function of pH. The rate constant for hydrolysis at pH 7.5 corresponds to a half-life of 16 min. The hydrolysis was too rapid to measure the rate at 37° C. Extrapolation using the rough rule that the rate will double for every 10° C. increase in temperature, gives an estimation of the half-life at pH 7.4 and 37° C. of 3 to 4 min. The rate constant increases with decreasing pH except for the transition from pH 10.4 to pH 9.0 where the rate constant decreases slightly. At pH 10.5 the solution appears purple, indicative of deprotonation at one of the hydroquinone functional groups. Hence, at this pH, at least some of the Doxaz has a different charge state. The higher rate at low pH is consistent with acid catalysis, probably assisting hydrolytic ring opening as the slow step. Which bond of the oxazolidine ring is broken first, the $CH_2$—O bond or the $CH_2$—NH bond, is unknown but may be relevant to a small portion of the biological activity. An intermediate from $CH_2$—NH bond cleavage would be an unlikely candidate for cross-linking DNA based upon the NMR and crystal structures of the virtual cross-link which all show a diaminomethane linkage. An intermediate from $CH_2$—O bond cleavage should be the same reactive intermediate produced by hydrolysis of DoxSF (FIG. 1). With an acid catalyzed mechanism, $CH_2$—O bond cleavage would be favored by protonation on oxygen, and $CH_2$—NH bond cleavage would be favored by protonation on nitrogen. This analysis of the ring opening reaction of Doxaz under hydrolytic conditions is relevant to a subsequent discussion of the direct reaction of Doxaz with DNA.

Figure 5:
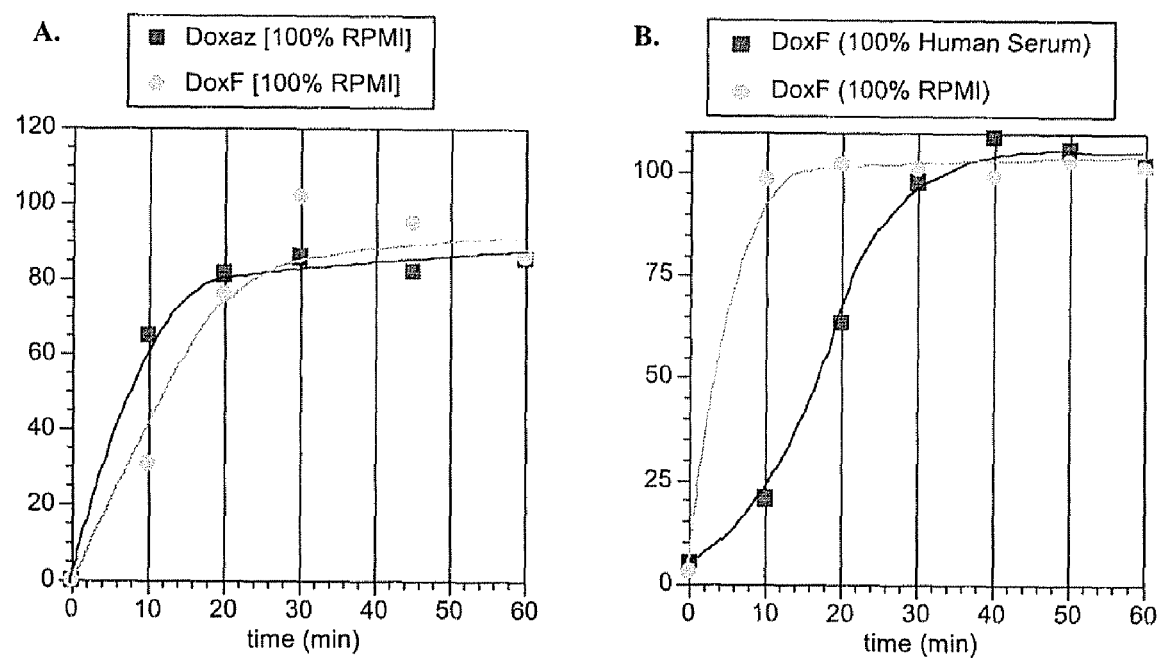
FIGS. 5A and 5B show the inhibition of the growth of MCF-7/Adr multidrug resistant breast cancer cells as a function of time for hydrolysis of Doxaz or DoxF at 37° C. Cells were treated with drug for 3 h, and cell growth in RPMI 1640 medium containing 10% FBS was measured at 5 days. The starting concentration in FIG. 5A was 1000 nM equivalents of Doxaz or DoxF in RPMI 1640 growth medium. The starting concentration in FIG. 5B was 100 nM equivalents of DoxF in RPMI 1640 growth medium or in 100% pooled human serum.

A functional measure of the rate of hydrolysis of Doxaz to Doxorubicin (and DoxF to Doxorubicin) is the effect of prehydrolysis as a function of time on the growth of MCF-7/Adr cells. This technique provides kinetic information because the concentration of Doxaz at time zero is 1 µM, and at this concentration the product of hydrolysis, Doxorubicin, has little activity. The result is shown in FIG. 5A starting with either Doxaz or DoxF at 1000 nM equivalents at 37° C. in RPMI 1640 media and in FIG. 5B starting with 100 nM equivalents of DoxF in either RPMI 1640 media or in 100% human serum. The media during cell growth was RPMI 1640 containing 10% fetal bovine serum in all the experiments in FIG. 5. The data in FIG. 5A give an estimate for the half-lives of Doxaz and DoxF at 37° C. in cell culture media. This estimate comes from the $IC_{50}$ value for cell growth inhibition by Doxaz and DoxF of approximately 2 nM and the requirement of nine hydrolytic half-lives to reach 2 nM Doxaz starting at 1000 nM equivalents. Note that after 9 half-lives no DoxF will be present because the rate of hydrolysis of DoxF to Doxaz is much faster than the rate of hydrolysis of Doxaz to Doxorubicin. FIG. 5A shows 50% growth inhibition by Doxaz after about 8 min for hydrolysis and by DoxF after about 13 min. From these times the half-life of Doxaz is estimated at 8/9 or approximately 1 min and the half-life of DoxF at 13/9 or approximately 1.5 min. From the data in FIG. 5B, human serum is estimated to extend the half-life of DoxF to about 3 min. For this calculation, six half-lives are required to reach 2 nM Doxaz from the starting concentration of 100 nM equivalents of DoxF. Human serum may double the life of DoxF through hydrophobic interactions with proteins.

Example 2

Doxazolidine Carbamate Prodrugs

Synthesis and Characterization

Analytical HPLC injections referenced below were onto an Agilent Zorbax 5 µm reverse-phase octadecylsilyl (ODS)

column, 4.6 mm i.d.×150 mm, eluting at 1.0 mL/min with a gradient of acetonitrile/20 mM triethylammonium acetate buffer pH 7.4, and the eluent was monitored at 280 and 480 nm. Electrospray mass spectra were measured with a Perkin-Elmer Sciex API III instrument (Norwalk, Conn.), equipped with an ion-spray source, at atmospheric pressure.

Figure 7:
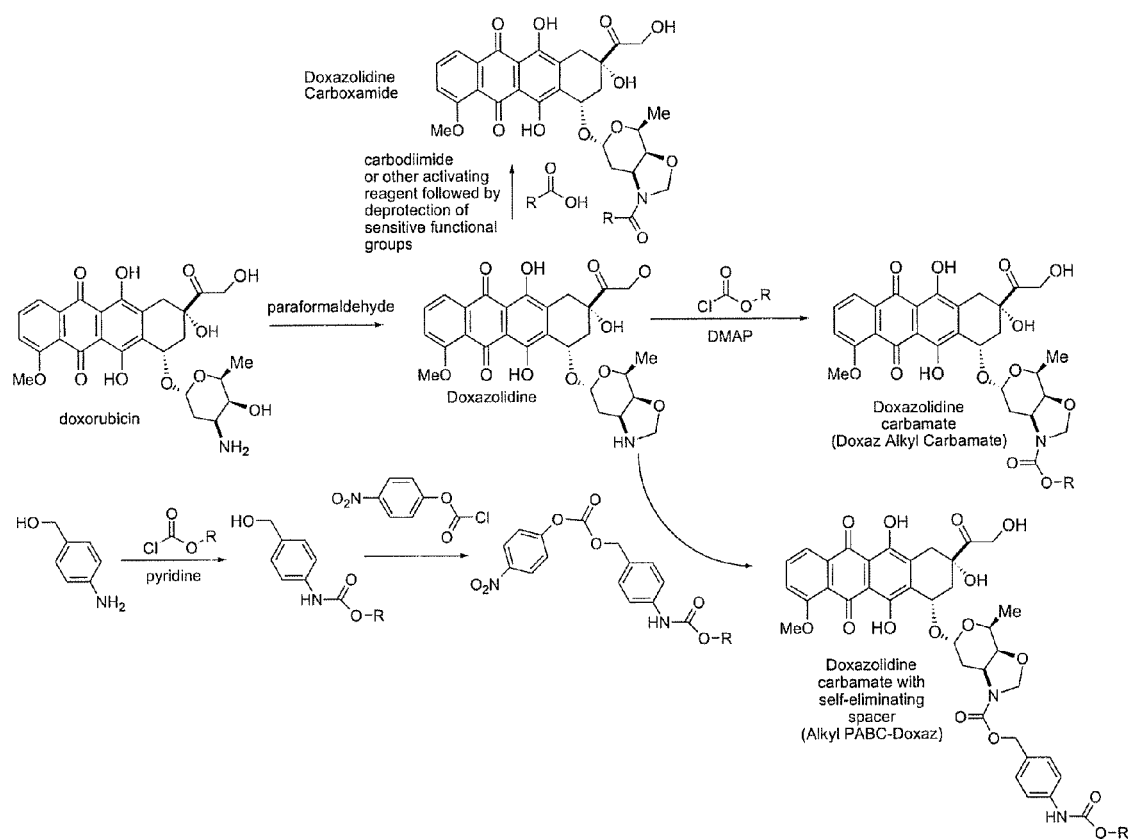
FIG. 7 shows the synthesis of Doxazolidine carboxamides, Doxazolidine carbamates, and Doxazolidine carbamates with a self-eliminating spacer.

Synthesis and characterization of simple Doxazolidine carbamates. The synthesis of simple Doxaz carbamates was achieved by addition of the modestly nucleophilic Doxaz to the desired alkyl chloroformate buffered by 1.1 equiv of dimethylaminopyridine (DMAP) or to the desired alkyl p-nitrophenyl carbonate (FIG. 7). The crude Doxaz carbamates were purified directly by radial chromatography and obtained in good yield. The structures were established from one and two dimensional NMR spectra and mass spectral molecular ions. Two-dimensional homonuclear NMR experimental data facilitated the assignment of proton NMR resonances. Resonances in the ambient temperature NMR spectra showed line broadening indicating conformational exchange at a rate similar to the NMR time scale.

Biological activity of simple Doxazolidine carbamates. Since the prodrug carbamates were designed to be activated by carboxylesterases CES1 (hCE1) and/or CES2 (hiCE), cell lines of interest were measured for expression of the respective mRNAs using reverse transcription (RT) followed by PCR (polymerase chain reaction). Cancer cell lines investigated included SHP-77 resistant small cell lung, DU-145 prostate, MCF-7 sensitive breast, MCF-7/Adr resistant breast, SK-HEP-1 liver, and Hep G2 liver cells. As a measure of possible cardiotoxicity, H9c2(2-1) rat cardiomyocytes were also investigated. Cardiotoxicity is relevant because the ultimate product of metabolism and subsequent hydrolysis of these carbamates is doxorubicin, which is cardiotoxic. The results of the RT-PCR showed that both liver cancer cell lines, SK-HEP-1 and Hep G2, strongly express the mRNA for CES2; however, only the Hep G2 cell line strongly expresses the mRNA for CES DU-145, MCF-7, and MCF-7/Adr cells express more CES2 than CES1, and SHP-77 cells express both enzymes, but in lesser amounts than Hep G2 cells. Additionally, the rat cardiomyocytes, H9c2(2-1), also express more CES2 than CES1.

Cell growth inhibition experiments initially focused on MCF-7, MCF-7/Adr, SK-HEP-1, and Hep G2 cancer cells as well as rat cardiomyocytes as a measure of cardiotoxicity and Vero cells (green monkey kidney cells) as an additional measure of normal cell toxicity. The butyl and pentyl carbamates inhibited the growth of MCF-7, MCF-7/Adr, and SK-HEP-1 cell lines with a 24 h drug treatment period with some selectivity for cancer cells over cardiomyocytes relative to growth inhibition by Dox as shown in Table 2. The ethyl carbamate with the least complex structure exhibited poor cancer cell growth inhibition. The relative inactivity of the ethyl carbamate may indicate that a substantial lipophilic interaction is required at the active site of the carboxylesterases to hold the Doxaz substrate. A control experiment showed that the pentyl carbamate is stable to hydrolysis in pH 7.4 buffer in the absence of cells or growth media over 24 h at ambient temperature monitoring the reaction by HPLC.

TABLE 2

Growth inhibition, $IC_{50}$ values reported as log of the molar concentration, of sensitive breast (MCF-7), resistant breast (MCF-7/Adr) and liver (SK-HEP-1 and Hep G2) cancer cells as well as a non-cancerous rat cardiomyocytes (H9c2(2-1)) and green monkey kidney cells (Vero) with 3 and/or 24 h drug treatments with Doxaz alkyl carbamates versus treatment with Doxorubicin or Doxaz.

| | | Drug | | | |
|---|---|---|---|---|---|
| Cell Line, Treatment Time | Doxorubicin | 1 Doxaz Ethyl Carbamate | 2 Doxaz Butyl Carbamate | 3 Doxaz Pentyl Carbamate | Doxaz |
| MCF-7, 3 h | $-6.5^a$ | >−6 | — | >−6 | $-8.5 \pm 0.03^b$ |
| 24 h | $-7.9 \pm 0.04$ | >1,000 | $-6.1 \pm 0.04$ | $-6.1 \pm 0.03$ | — |
| MCF-7/Adr, 3 h | $-5.2 \pm 0.1$ | $-5.3 \pm 0.04$ | — | — | $-8.5 \pm 0.03^b$ |
| 24 h | $-5.6 \pm 0.1$ | >−5 | $-6.2 \pm 0.3$ | $-6.0 \pm 0.09$ | — |
| SK-HEP-1, 3 h | $-7.0 \pm 0.1$ | >−6 | — | >−6 | $-8.4 \pm 0.1$ |
| 24 h | $-7.3 \pm 0.2$ | >−6 | $-6.4 \pm 0.2$ | $-6.7 \pm 0.1$ | — |
| Hep G2, 3 h | $-6.7 \pm 0.09$ | >−6 | — | >−6 | $-8.0 \pm 0.08$ |
| 24 h | $-7.5 \pm 0.1$ | >−6 | $-6.7 \pm 0.3$ | $-6.5 \pm 0.3$ | — |
| H9c2(2-1), 3 h | $-7.5 \pm 0.2$ | $-5.8 \pm 0.2$ | — | — | $-7.5 \pm 0.2$ |
| 24 h | $-7.7 \pm 0.3$ | — | $-5.8 \pm 0.2$ | $-6.6 \pm 0.1$ | — |
| Vero, 3 h | $-6.0 \pm 0.02$ | — | — | $-5.4 \pm 0.1$ | $-8.2 \pm 0.04$ |
| 24 h | $-6.3 \pm 0.08$ | — | $-6.3 \pm 0.1$ | $-5.3 \pm 0.01$ | $-8.1 \pm 0.3$ |

Viability of cells was assayed with crystal violet, except viability of H9c2(2-1) cells treated for 3 h and of Vero cells treated for 3 or 24 h which was assayed with MTT.

Figure 4:
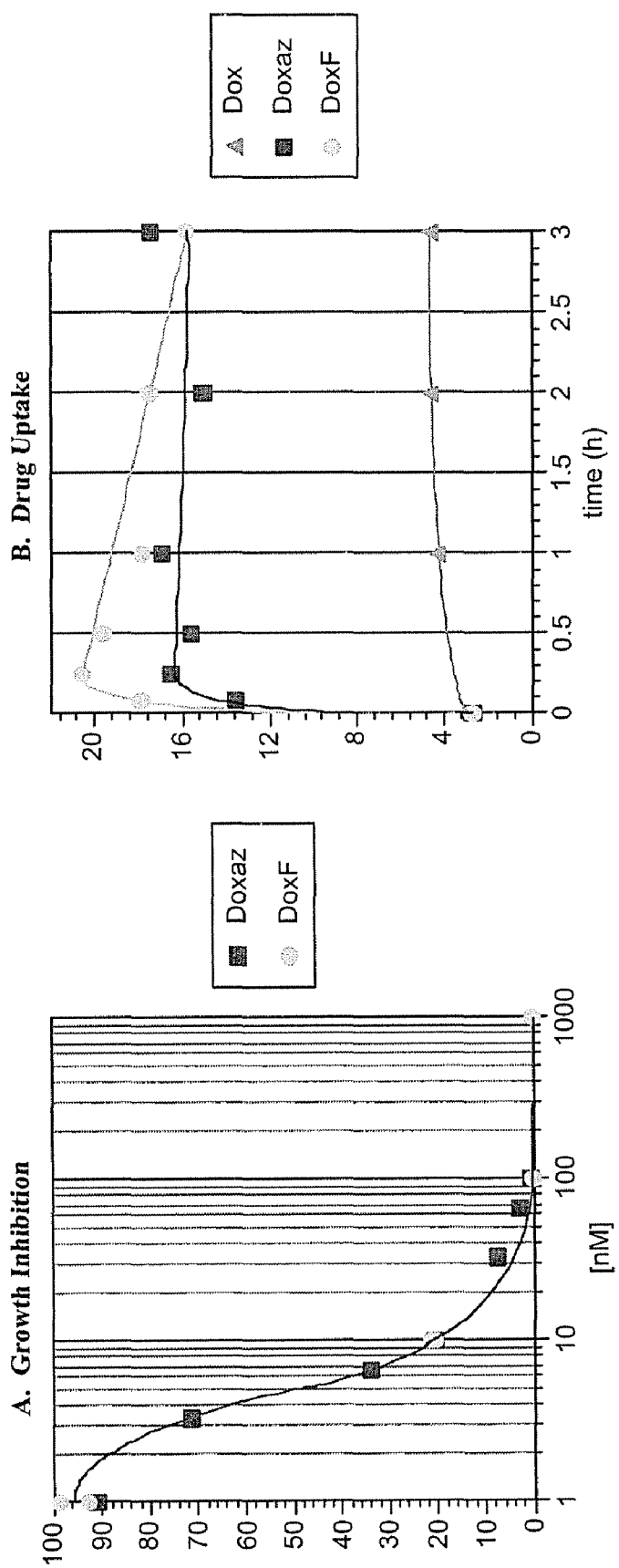
FIG. 4A shows inhibition of growth of multidrug resistant MCF-7/Adr breast cancer cells with Doxaz and DoxF as a function of concentration. The concentration of DoxF is in nM equivalent to correct for DoxF functioning as a prodrug for two equivalents of Doxaz.
FIG. 4B shows the relative fluorescence of the Doxorubicin chromophore in MCF-7/Adr cells treated with 500 nM Doxaz, 500 nM equivalents DoxF, or 500 nM Doxorubicin as a function of time after inoculation of the cell culture, measured by flow cytometry.

Uptake of the pentyl carbamate relative to uptake of Dox was measured by flow cytometry, monitoring fluorescence of the Dox fluorophore as a measure of drug in cells. The measurements were performed over a period of 3 h in the presence and absence of fetal bovine serum, and the results are shown in FIG. 4. Clearly, the pentyl carbamate was taken up at a higher level and more rapidly than Dox. Further, the presence of 10% fetal bovine serum decreased the uptake of doxorubicin and the pentyl carbamate by about 25%. The more rapid uptake of the pentyl carbamate in the presence and absence of serum probably reflects its increased hydrophobicity relative to that of doxorubicin which is a cation at physiological pH. Increased hydrophobicity may also be the explanation for the effect of serum on the uptake of the carbamate; namely, the carbamate binds to serum proteins reducing drug uptake.

Synthesis and characterization of Doxazolidine carbamates with self-eliminating spacer. The growth inhibition data together with experience with prodrugs suggested drug efficacy might be improved by adding a self-eliminating spacer between the alkyl carbamate functionality and the anthracycline. This could present the lipophilic carbamate to the enzyme with significantly less steric bulk and increase the rate of enzymatic hydrolysis. The spacer was incorporated by reacting PABA with the desired chloroformate followed by conversion to the p-nitrophenyl carbonate ester and reaction with Doxaz. The structures again were established from NMR spectra and mass spectral molecular ions.

Biological activity of Doxazolidine carbamates with self-eliminating spacer. Growth inhibition experiments with butyl and pentyl carbamates bearing the PABC self-eliminating spacer focused on Hep G2 liver cancer cells that strongly express both CES1 and CES2 and SK HEP-1 cells that express significantly more CES2 than CES1. SHP-77 small cell lung cancer cells were also of interest because they express modest amounts of both enzymes. Inhibition of the growth of cardiomyocytes was used as a measure of cardiotoxicity, and inhibition of the growth of Vero cells, green monkey kidney cells, was again used as another measure of toxicity to normal cells. Clearly, both the butyl and pentyl carbamates with PABC spacer are more active than the simple carbamates as shown in Table 3. They also show more activity against the cancer cells that express higher levels of CES1. Of particular note is the higher activity against Hep G2 cells than against SK-HEP-1 cells. This suggests that CES1 is more active than CES2. Pentyl PABC-Doxaz also shows more than one order of magnitude lower toxicity to cardiomyocytes and Vero cells than to Hep G2 and SHP-77 cells. The low toxicity of pentyl PABC-Doxaz to cardiomyocytes relative to the toxicity of Dox is encouraging and consistent with the low level of expression of CES1 in cardiomyocytes.

Formula V (aFK-PABC-PABC-Doxaz; Compound 10 of FIG. 8) having an elongated spacer was also synthesized for comparison of enzymatic efficiency.

Figure 9:
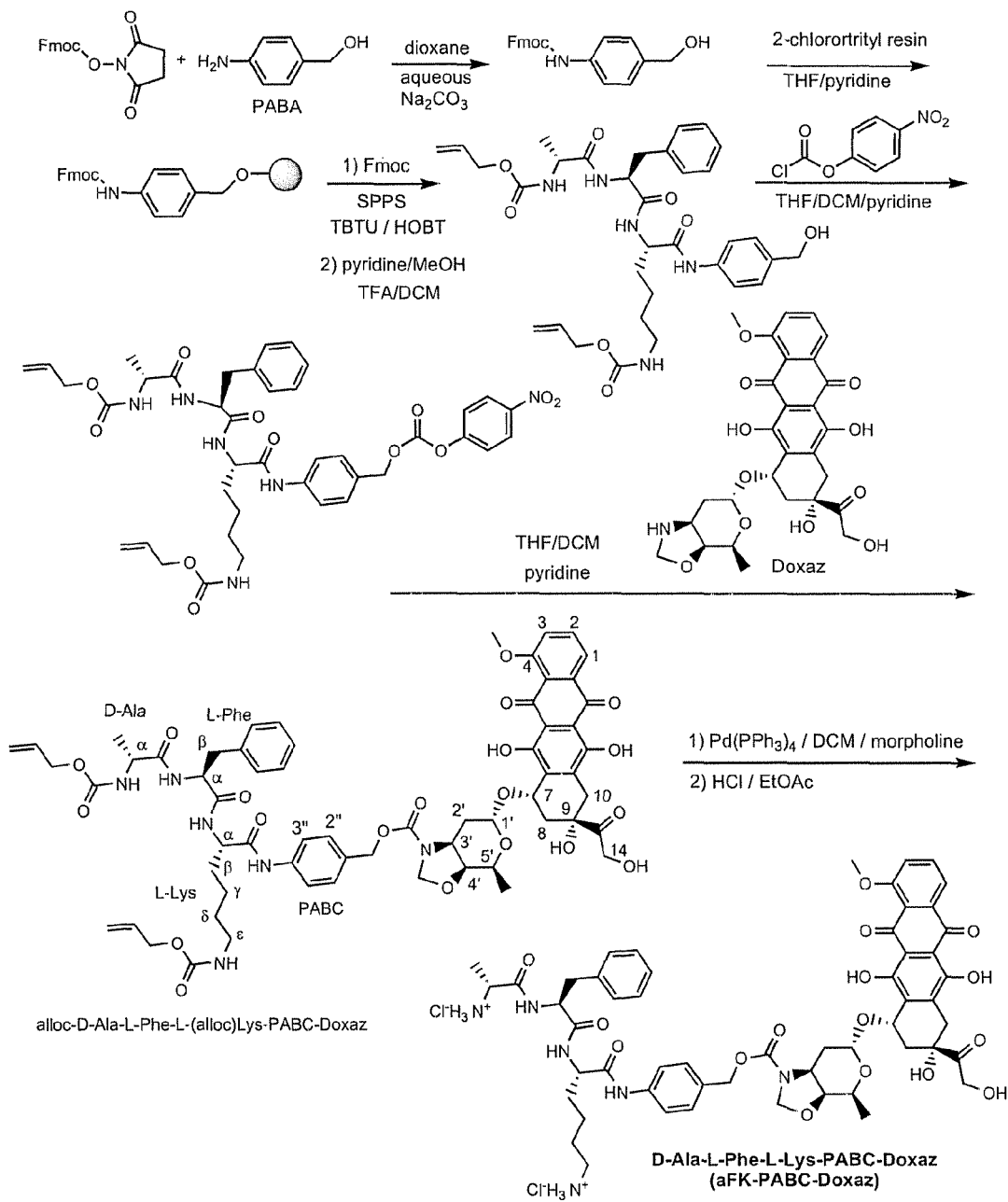
FIG. 9 shows the synthesis of D-Ala-L-Phe-L-Lys-PABC-Doxaz (aFK-PABC-Doxaz). Abbreviations: alloc, allyloxycarbonyl; DCM, dichloromethane; Doxaz, doxazolidine; Fmoc, fluorenylmethyloxycarbonyl; HOBT, N-hydroxybenzotriazole; PABC, p-aminobenzyloxycarbonyl; SPPS, solid phase peptide synthesis; TBTU, 2-(1H-benzotriazole-1-yl)-1,1,3,3-tetramethyluronium hexafluorophosphate; TFA, trifluoroacetic acid; THF, tetrahydrofuran.

Using Formula IV (aFK-PABC-Doxaz; Compound 10) as an example, another strategy for the synthesis of Formulas IV and V is shown in FIG. 9. Solid phase Fmoc peptide synthesis methodology was used with the Fmoc-PABA directly attached to the resin via its alcohol functional group, and the protected amino acids were added sequentially from the amino group of the PABA. The $\epsilon$-amino of L-Lys and the amino terminus of D-Ala were protected using the orthogonal allyloxycarbonyl group (alloc). The first coupling of the alloc-L-Lys required additional reaction time because of the low reactivity of the anilino functional group. After cleavage of alloc-D-Ala-L-Phe-L-(alloc)Lys-PABA from the resin, its benzyl alcohol was activated with p-nitrophenylchloroformate, and the PNP derivative coupled to a preformed mixture of Doxazolidine and Doxoform. The yield of alloc-D-Ala-L-Phe-L-(alloc)Lys-PABC-Doxaz was independent of the composition of this mixture. The alloc protecting groups where removed with palladium tetrakistriphenylphosphine, and Formula IV (aFK-PABC-Doxaz) was isolated as its bis-hydrochloride salt by protonation with anhydrous hydrogen chloride in ethyl acetate. The structures of intermediates and the final product were established by high resolution NMR and mass spectrometry. In particular, alloc-D-Ala-L-Phe-L-

TABLE 3

Cell growth inhibition values ($IC_{50}$) expressed in log of molar concentrations for Doxaz alkyl carbamates and alkyl PABC-Doxaz compounds compared with Doxorubicin for 24 h drug treatment.

| Cell Line | Doxorubicin | 2 Doxaz Butyl Carbamate | 4 Butyl PABC-Doxaz | 3 Doxaz Pentyl Carbamate | 5 Pentyl PABC-Doxaz |
|---|---|---|---|---|---|
| MCF-7 | −7.9 ± 0.04 | −6.1 ± 0.04 | −4.1 ± 0.3 | −6.1 ± 0.03 | −5.6 ± 0.3 |
| MCF-7/Adr | −5.6 ± 0.1 | −6.2 ± 0.3 | −5.9 ± 0.06 | −6.0 ± 0.09 | −6.5 ± 0.06 |
| DU-145 | −7.5 ± 0.08 | −6.4 ± 0.02 | −6.3 ± 0.3 | −6.0 ± 0.04 | −6.7 ± 0.07 |
| SHP-77 | −6.9 ± 0.05 | −6.6 ± 0.3 | −7.1 ± 0.1 | −6.3 ± 0.3 | −7.3 ± 0.1 |
| HepG2 | −7.5 ± 0.1 | −6.7 ± 0.3 | −7.7 ± 0.03 | −6.5 ± 0.3 | −7.3 ± 0.2 |
| SK-HEP-1 | −7.3 ± 0.2 | −6.4 ± 0.2 | −5.8 ± 0.04 | −6.7 ± 0.1 | −6.0 ± 0.06 |
| H9c2(2-1) | −7.7 ± 0.3 | −5.8 ± 0.2 | −7.2 ± 0.2 | −6.6 ± 0.1 | −6.2 ± 0.2 |
| Vero | −6.3 ± 0.08 | −6.3 ± 0.1 | −6.1 ± 0.08 | −5.3 ± 0.01 | −6.0 ± 0.04 |

Figure 3:
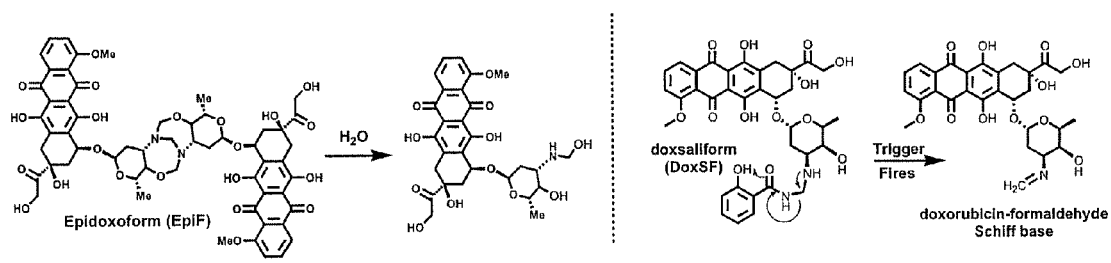
FIG. 3 shows the structures of pro-drugs Epidoxoform (EpiF) and DoxSF and reactions to release monomeric forms that could cross-link DNA. Neither EpiF nor DoxSF release Doxaz.

Cancer cells are defined in the legends to Table 1 and FIG. 3. Growth inhibition of cardiomyocytes (H9c2(2-1)) is a measure of cardiotoxicity, and growth inhibition of Vero cells (green monkey kidney cells) is a second measure of toxicity to normal cells. Viability of cells was assayed with crystal violet except the viability of Vero cells which was assayed with MTT.

Uptake of pentyl PABC-Doxaz and Dox by multidrug resistant MCF-7/Adr breast cancer cells and SK-HEP-1 liver cancer cells in the presence of fetal bovine serum was determined by flow cytometry using drug fluorescence as a measure of drug in cells. Pentyl PABC-Doxaz is taken up much better by both cell lines than Dox.

Example 3

Synthesis and Activity of Plasmin-Activated Doxazolidine Prodrugs

Figure 8:
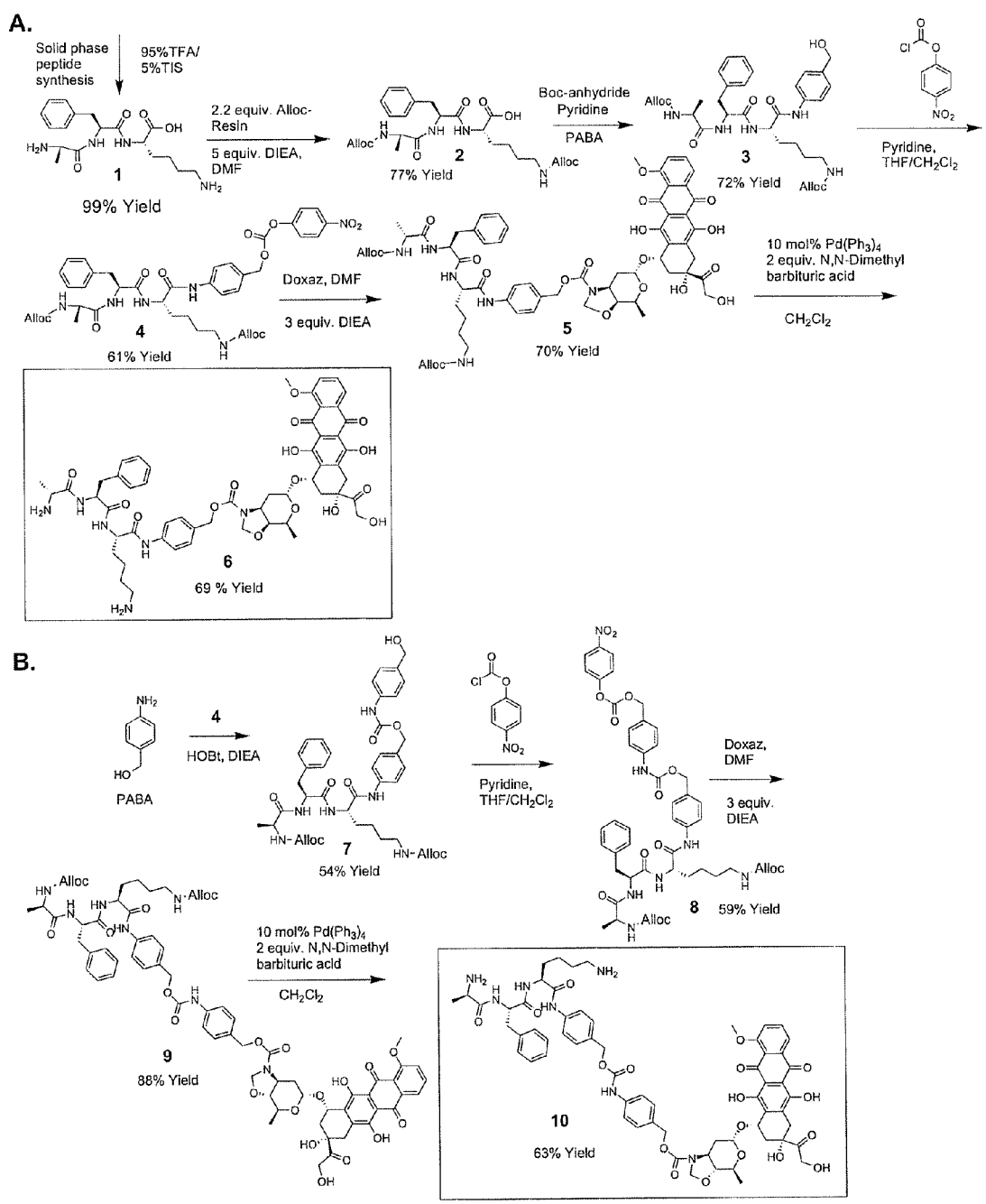
FIG. 8 shows the synthesis of two plasmin-activated Doxaz prodrugs (structures 6 and 10).

Synthesis. Plasmin-activated prodrugs of the present invention were synthesized starting with solid phase peptide synthesis, as shown in FIGS. 8 and 9. The synthesis of the prodrug compounds of Formulas IV and V of the present disclosure (corresponding to compounds 6 and 10 of FIG. 8, respectively) was facilitated by the fact that the final amine deprotection could be carried out under mild reaction conditions after formation of the peptide/Doxaz carbamate.

(alloc)Lys-PABC-Doxaz was extensively studied by two dimensional NMR including homonuclear COSY, NOSY, HSQC and HMBC spectra to assign the proton resonances and most of the carbon resonances.

Both Formula IV and V exhibit excellent water solubility and much improved stability (>6 hours) with respect to hydrolysis of the oxazolidine ring in aqueous media at pH 7.4.

Plasmin activation and release of active Doxaz. Plasmin cleaves prodrug Formulas IV and V (aFK-PABC-Doxaz and aFK-PABC-PABC-Doxaz) at the anilide functional group between the Lys and PABC groups. The resulting aniline derivatives should then undergo spontaneous 1,6-elimination of p-aminobenzoquinone methide to give the carbamic acid of doxazolidine. Spontaneous decarboxylation of the carbamic acid then gives Doxaz.

Both Formulas IV and V were incubated with 15 μg/ml human plasmin and monitored by HPLC at 37° C. Just 4 min after the addition of plasmin, 20 percent of compound 10 was converted to Doxaz and roughly 50% of that Doxaz had hydrolyzed to Doxorubicin. Within 23 minutes, nearly all of the prodrug was converted to Doxaz and subsequently hydrolyzed to Doxorubicin. Scheeren and co-workers reported that the equivalent Doxorubicin prodrug ST-9905 exhibited similar kinetics and showed no conversion to Doxorubicin after incubation in bovine serum for 3 days.

Activity of plasmin-activated prodrugs. In spite of Doxaz's short half-life, both plasmin-activated prodrugs of Formula IV and V exhibit superior cancer cell growth inhibition ($IC_{50}$=0.005 μM) in the presence of 15 μg/ml plasmin for both sensitive and multidrug-resistant cancer cells as shown in Table 4.

aFK-PABC-Doxaz and aFK-PABC-Dox, in some cases by more than a log. Addition of 0.01 unit/mL plasminogen increases the activity of aFK-PABC-Doxaz on average by 0.3 log. Rat cardiomyocytes are susceptible to both Dox and Doxaz but less susceptible to either aFK-PABC-Doxaz or aFK-PABC-Dox except upon addition of plasmin. The cell growth inhibition experiments support aFK-PABC-Doxaz functioning as it was designed to function and with a log higher activity than aFK-PABC-Dox.

TABLE 4

Cancer cell and cardiomyocytes growth inhibition ($IC_{50}$) by Doxaz prodrug Formula IV and V, +plasmin, and +aprotinin versus Doxorubicin and Doxorubicin prodrug aFK-PABC-Doxorubicin (ST-9905).

| Drug | MCF-7 | MCF-7 + plasmin (aprotinin) | MCF-7/Adr | MCF-7/Adr + plasmin (aprotinin) | MDA-MB-435 + plasmin (aprotinin) | DU-145 + plasmin (aprotinin) | Rat Cardio. + plasmin (aprotinin) |
| --- | --- | --- | --- | --- | --- | --- | --- |
| Doxorubicin | 0.3 | 0.3 | 10 | 20 | 0.15 | 0.3 | 0.02 |
| ST-9905 | — | 0.45 (0.6) | — | 0.6 (>3) | — | — | 1.3 (>3) |
| Formula IV | 0.05 | 0.005 | 0.1 | 0.01 (0.3) | 0.24 0.04 0.24 | 0.16 0.006 (0.19) | — 0.04 (1) |
| Formula V | 0.06 | 0.009 | 0.1 | 0.01 | — | — | — (1) |

All values are expressed as μM concentrations.

A critical discovery of this research is that both the compounds of Formula IV and V have $IC_{50}$ values of 1 μM against rat cardiomyocytes in the presence of aprotinin, a plasmin inhibitor, whereas Doxoruhicin's $IC_{50}$ value is 0.02 μM. In vivo, the plasmin inhibitors prevalent throughout the bloodstream prevent the cardiotoxic side effects of the prodrugs. This indicated that the plasmin-activated prodrug Formulas IV and V were very promising prodrugs possessing the superior cytotoxicity and reduced cardiotoxicity of Doxaz relative to Doxorubicin.

A more thorough characterization of the growth inhibition of a variety of cancer cells as well as rat cardiomyocytes by Formula IV (aFK-PABC-Doxaz) was evaluated in comparison with inhibition of growth by Doxaz, Dox and aFK-PABC-Dox. Cells were treated with drug for 3 h and colony growth was measured at 3 to 5 days when cells reached about 80% confluence. The cancer cells included one prostate cancer cell line (DU-145), three related breast cancer cell lines (MCF-7, MCF-7/Adr, and MCF-7 uPA), and one pancreatic cancer cell line (Mia PaCa-2). The breast cancer cell lines represent the multi-drug resistant (MDR) phenotype with MCF-7/Adr cells and a cell line that is transfected with the gene for urokinase plasminogen activator (uPA), the primary enzyme responsible for cleavage of plasminogen to plasmin. Rat cardiomyocytes served as a model for comparison of drug cardiotoxicity. Growth inhibition was also measured with added plasmin. aFK-PABC-Doxaz inhibited the growth of most of the cancer cells 0.5 log or more better than did aFK-PABA-Dox. Although not as dramatic, this differential response paralleled the differential response between Doxaz and Dox which is approximately two logs except for the MDR expressing, MCF-7/Adr cells which show more than three logs differential response. In fact, aFK-PABC-Doxaz, but not aFK-PABC-Dox, shows significant activity against these MDR expressing cells. Addition of 0.01 unit/mL of plasmin has no effect on the activity of Dox but increases the activity of both Example 4

Doxazolidine Prodrugs Activated by β-Glucuronidase

Synthesis. The synthesis of a Doxazolidine-glucuronide prodrug conjugate that is activated by β-glucuronidase (Doxaz-PABC-glucuronide) is shown in FIG. 10. The oxazolidine ring resembles an acetal in that it is stable under basic conditions but is hydrolyzed by dilute acid. With this in mind, hydrolysis of the three glucuronate acetate groups to give Doxaz-PABC-glucuronide will be performed with 3 equivalents of sodium methoxide at 0° C. All compounds will be purified by silica gel chromatography, radial chromatography, or preparative reverse-phase HPLC. All intermediates will be characterized by $^1$H NMR, $^{13}$C NMR and MS, and their state of purity established by analytical reverse-phase HPLC. Final products will be characterized using mass spectrometry, one and two dimensional NMR, reverse-phase HPLC, and elemental analysis.

Example 5

Doxazolidine Prodrugs Activated by Carboxypeptidase G2

Synthesis. The synthesis of a Doxazolidine-glutamic acid prodrug conjugate that is activated by carboxypeptidase G2 (Doxaz-COBAC-Glu, Formula VII) is shown in FIG. 10.

Bis-allyl t-butyldiphenylsilyloxy-p-benzylaminocarbonyl-L-glutamate (4). To a stirred solution of 400 mg (1.03 mmol) of t-butyldiphenylsilyloxy-p-benzylisocyanate (2) in 2.0 mL of THF, was added dropwise, a solution containing 1.05 mmol of triethylamine and 234 mg (1.03 mmol) of bis-allyl L-glutamate (3) in 2.0 mL of THF over the course of 30 min at room temperature. After 5 h the reaction was complete. The precipitate was filtered off and the filtrate concentrated under vacuum. The resulting yellow oil was dissolved in 25 mL of EtOAc and washed with 25 mL of distilled water, 25 mL of HCl (1%), 25 mL, saturated Na$_2$CO$_3$ and 25 mL×2 of distilled water. The organic layer was dried over anhydrous sodium sulfate, filtered and concentrated, resulting in a pale yellow oil. Radial chromatography using a 4 mm plate eluted with 2:1 EtOAc/cyclohexane resulted in the isolation of 418 mg of a pale yellow oil (4) in 66% yield.

Alternative method for 4. A three necked round bottom flask equipped with a stir bar and addition funnel was charged with 14.7 mL of a 0.300 M (4.40 mmol) solution of 3 in toluene. To this mixture, 0.436 g (1.47 mmol) of triphosgene was added in one portion at −78° C. The addition funnel was charged with 0.613 mL (4.40 mmol) of triethylamine in 10 mL of toluene. This solution was added dropwise over 40 min. The reaction mixture was then allowed to reach room temperature, and monitored by IR spectroscopy. The formation of an isocyanate peak at 2254 cm$^{-1}$ reached a maximum in 120 min. The addition funnel was then charged with 1.55 g (4.30 mmol) of t-butyldiphenylsilyloxy-p-benzylamine (1) in 9.35 mL of toluene and 0.613 (4.40 mmol) triethylamine. This solution was added dropwise over 30 min. The resulting reaction mixture was monitored by IR specrospcopy for the disappearance of the isocyanate peak, and was complete after 8 h. The reaction mixture was filtered, concentrated, dissolved in 60 mL EtOAc and washed with 60 mL distilled water, 60 mL of HCl (1%), 60 mL of saturated Na$_2$CO$_3$ and 60 mL×2 of distilled water. The organic layer was dried over anhydrous sulfate, filtered and concentrated, resulting in a white solid immersed in a pale yellow oil. Radial chromatography using a 4 mm Chromotatron plate eluted with 1:5 EtOAc to cyclohexane resulted in the isolation of 4 as a pale yellow oil in 54% yield.

Bis-allyl hydroxy-p-benzylaminocarbonyl-L-glutamate (5). A 1.0 M solution of tetrabutylammonium fluoride (1.0 mL) in THF was transferred to a dry flask under argon. Acetic acid was added dropwise to adjust the pH of the solution to approximately 5 as evidenced by wide range pH paper. A 0.1 mL aliquot (0.1 mmol TBAF) of this acidified solution was transferred under argon to a dry flask containing 20.0 mg (0.033 mmol) of the protected alcohol 4 in 0.5 mL of freshly distilled THF. The reaction was left to stir under a static argon. As evidenced by silica gel TLC eluted with 1:1 EtOAc/cyclohexane. The reaction was complete after 48 h. The reaction mixture was concentrated and dissolved in 20 mL of EtOAc. This organic layer was extracted 3 times with distilled water (45 mL total), dried with anhydrous Na$_2$SO$_4$, filtered and concentrated. The resulting pale yellow oil was purified by radial chromatography using 2:1 EtOAc/cyclohexane. A pale yellow oil (8.5 g) was isolated, corresponding to a yield of 75%.

Bis-allyl p-nitrobenzyloxycarbonyloxy-p-benzylaminocarbonyl-L-glutamate (6). Alcohol 5 (8.50 mg (0.0226 mmol)) was left under high vacuum for >24 h. This dry flask was purged with argon, and to it added 1 mL of freshly distilled THF and 1 mL of freshly distilled CH$_2$Cl$_2$ to bring the alcohol concentration to 0.0113 M. To this was added 11.5 mg (0.0588 mmol) of 4-nitrophenylmethylchloroformate and 4.75 µl, (0.0565 mmol) of freshly distilled pyridine. The reaction was left to stir under static argon for 48 h. The reaction mixture was concentrated then dissolved in 15 mL of EtOAc. This organic layer was washed twice with 15 mL, of Brine, dried over anhydrous sulfate and concentrated. The resulting yellow oil, which solidified on standing, was purified by radial chromatography in 2:1 EtOAc/cyclohexane, yielding a white solid in 32% yield.

Bis-allyl N-Doxazolidinylcarbonyloxy-p-benzylaminocarbonyl-L-glutamate (7). To a dry round bottom flask is added the carbonate ester 6 and 1.5 to 2.9 equiv of doxoform in minimal dry DMSO. The mixture is stirred under argon and the reaction monitored by HPLC. After 4 days the carbonate ester 6 is consumed, and the solution divided into two equal portions. Each portion is then diluted with 100 mL of PBS causing the precipitation of all compounds joined to doxorubicin. The precipitate is pelletized by centrifugation at 3000×g and 10° C. for 10 min to remove p-nitrophenol. This is repeated eight times using 80 mL of PBS each time, followed once with 80 mL of distilled water to remove any salts. The crude product from each portion is purified by silica gel radial chromatography injecting the product in and eluting with 30:1 CHCl$_3$:MeOH.

N-Doxazolidinylcarbonyloxy-p-benzylaminocarbonyl-L-glutamic acid (Doxaz-COBAC-Glu, Formula VII; 8 FIG. 10). To a centrifugation tube containing 10 mg of protected prodrug 7 is added 3 mL of a 2:1 mixture of dichloromethane/THF. The solvent is degassed with argon, then 10 equiv of dry morpholine is added followed by 0.2 to 0.5 equiv of tetrakistriphenylphosphine Pd$^0$. The reaction is stirred under argon for 1 h in the dark. The stir bar is removed and the reaction mixture is centrifuged at 3000×g for 15 min. The supernatant is removed and the remaining solids are dissolved in chloroform/methanol, and purified by radial chromatography. The solid product is then dried under high vacuum for 18 h to yield prodrug 8.

Example 6

Doxazolidine Prodrugs Activated by β-Lactamase

Figure 11:
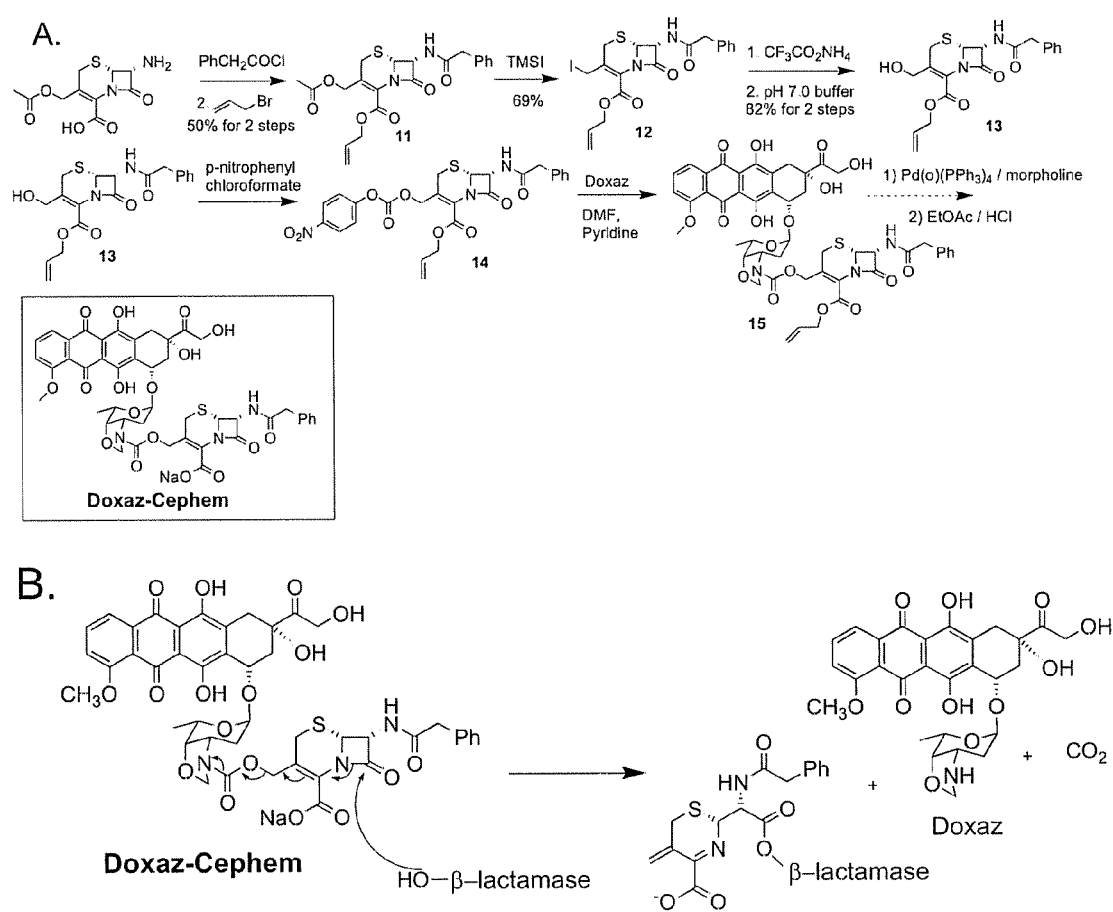
FIG. 11A depicts the synthesis of the prodrug Doxaz-Cephem of the present invention. The abbreviations used in this synthetic scheme: DMF, dimethylformamide; TMSI, trimethylsilyliodide.
FIG. 11B depicts an activation mechanism of Doxaz-Cephem by β-lactamase, releasing Doxaz after decarboxylation.

Synthesis. The synthesis of a Doxazolidine-cephalosporin prodrug conjugate that is activated by β-lactamase (Doxaz-Cephem, Formula VIII) is shown in FIG. 11.

p-Nitrophenyl carbonate of cephalosporin 14 (FIG. 11). To a 25 ml round bottom flask was added alcohol cephalosporin alcohol 13 (0.3 mmol) was 6 mg of dichloromethane followed by 38 µL of pyridine. This solution was stirred under nitrogen and to it was added 90.7 mg of p-nitrophenyl chloroformate. The solution was stirred under static nitrogen for 24 h. At this point distilled water was added and washed in a separatory funnel. This was followed by washes with saturated sodium carbonate and then saturated sodium chloride. The organic layer was dried over sodium sulfate, filtered and then concentrated under low vacuum followed by high vacuum. The resulting oil was purified using radial silica gel chromatography eluting with 160:1 chloroform:methanol. The yield for this reaction was from 50% to 70% and the structure was established by NMR spectroscopy.

Allyl Doxaz-Cephem 15 (FIG. 11). To a 10 mL dry round bottom flask under argon was added p-nitrophenyl carbonate of cephalosporin 14 followed by a saturated solution of DoxF in DMSO. The ratio of DoxF was 2:1 with respect to the cephalosporin derivative. The reaction mixture was stirred for four days under static argon at which point the solution was concentrated. The resulting mixture was washed 3 to 5 times with saturated sodium carbonate and concentrated. The resulting solid was purified using radial silica gel chromatography eluting with 30:1 chloroform:methanol to yield coupled product allyl Doxaz-Cephem 15 in 10% yield. The product was characterized by NMR spectroscopy. The spectral data were obtained at 50° C. because the compound exhibited conformational dynamics on the NMR time scale. A byproduct with the double bond of the cephalosporin ring migrated was isolated in 15% yield from the radial chromatography of the reaction mixture and was also characterized by one and two dimensional NMR spectroscopy. The spectral data were again obtained at 50° C. because the compound exhibited conformational dynamics on the NMR time scale.

Doxaz-Cephem (Formula VIII). To a centrifugation tube containing 10 mg of allyl Doxaz-Cephem 15 is added 3 mL of a 2:1 mixture of dichloromethane/THF. The solvent is degassed with argon, then 10 equiv of dry morpholine is added followed by 0.2 to 0.5 equiv of tetrakistriphenylphosphine Pd⁰. The reaction is stirred under argon for 1 h in the dark. The stir bar is removed and the reaction mixture is centrifuged at 3030×g for 15 min. The supernatant is removed and the remaining solids suspended in ethyl acetate. The suspension is acidified with 0.5 M dry HCl in ethyl acetate then centrifuged. The acidic supernatant is removed, fresh ethyl acetate is added, and then the suspension centrifuged again. This is repeated a total of four times. The solid product is then dried under high vacuum for 18 h to yield Doxaz-Cephem (Formula VIII) and characterized by NMR spectroscopy and mass spectrometry.

Activation. The activation of Doxaz-Cephem by the enzymatic action of β-lactamase to release the active Doxaz from the cephalosporanic acid residue is depicted in FIG. 11.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. An anthracycline-formaldehyde compound having the chemical formula:

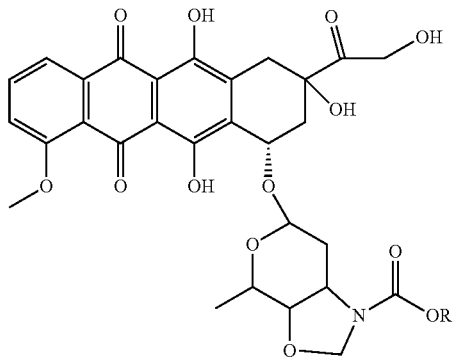

or a pharmaceutically-acceptable salt thereof, wherein R is a cycloalkyl group having between 3 and 20 carbon atoms, or an aryl group.

2. An anthracycline-formaldehyde compound having the chemical formula:

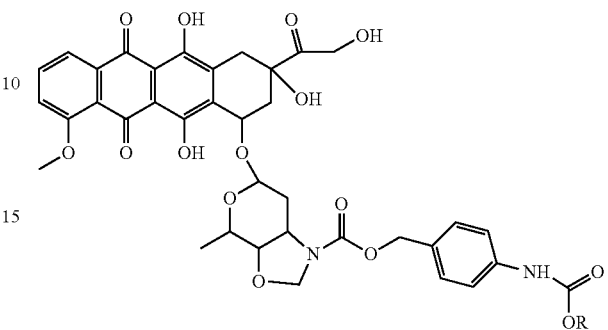

or a pharmaceutically-acceptable salt thereof, wherein R is an alkyl group having between 1 and 100 carbon atoms.

3. An anthracycline-formaldehyde compound having the chemical formula:

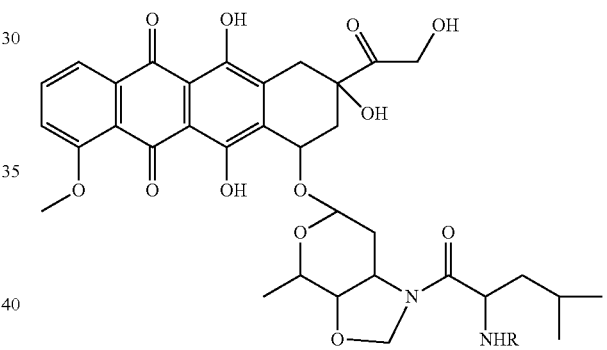

or a pharmaceutically-acceptable salt thereof, wherein R is a molecule removed by an enzyme present in a cancer cell.

4. An anthracycline-formaldehyde compound having the chemical formula:

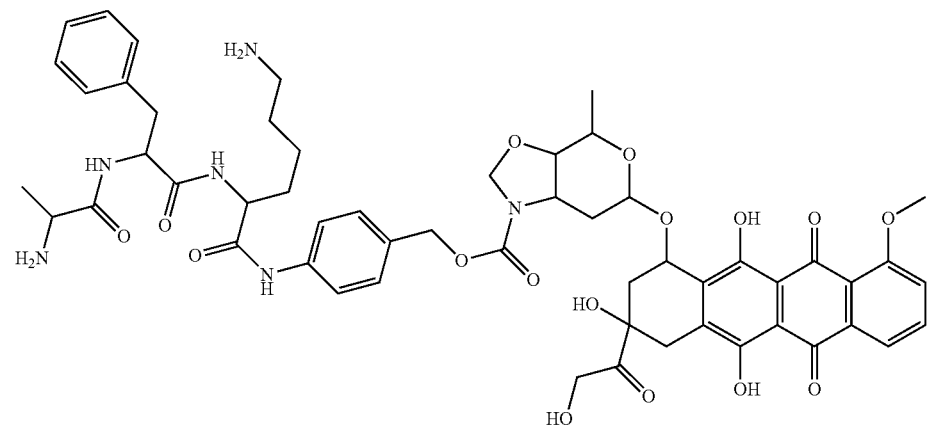 [SMILES: COc1cccc2c1C(=O)c1c(O)c3c(c(O)c1C2=O)CC(O)(C(=O)CO)CC3OC1CC2C(OCN2C(=O)OCc2ccc(NC(=O)C(CCCCN)NC(=O)C(Cc3ccccc3)NC(=O)C(C)N)cc2)C(C)O1]

or a pharmaceutically-acceptable salt thereof.

5. An anthracycline-formaldehyde compound having the chemical formula:
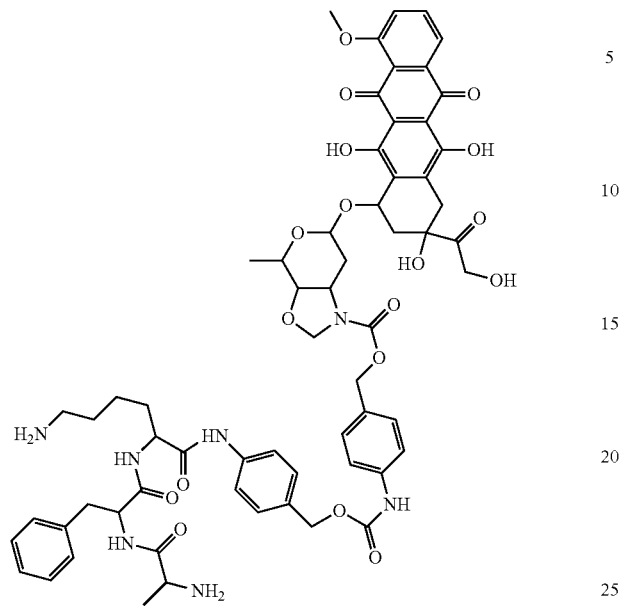
or a pharmaceutically-acceptable salt thereof.
6. An anthracycline-formaldehyde compound having the chemical formula:
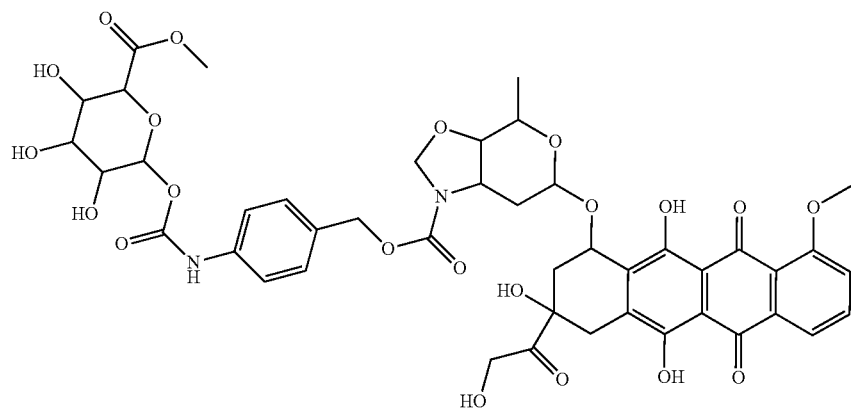 [SMILES: COC(=O)C1OC(OC(=O)Nc2ccc(COC(=O)N3COC4C(C)OC(OC5CC(O)(C(=O)CO)Cc6c(O)c7c(c(O)c65)C(=O)c5c(OC)cccc5C7=O)CC43)cc2)C(O)C(O)C1O]
or a pharmaceutically-acceptable salt thereof.
7. An anthracycline-formaldehyde compound having the chemical formula:
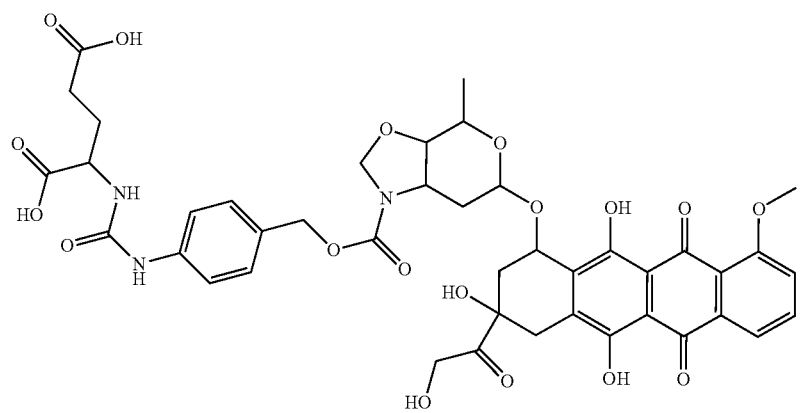 [SMILES: COc1cccc2c1C(=O)c1c(O)c3c(c(O)c1C2=O)CC(O)(C(=O)CO)CC3OC1CC2C(OCN2C(=O)OCc2ccc(NC(=O)NC(CCC(=O)O)C(=O)O)cc2)C(C)O1]
or a pharmaceutically-acceptable salt thereof.

8. An anthracycline-formaldehyde compound having the chemical formula:
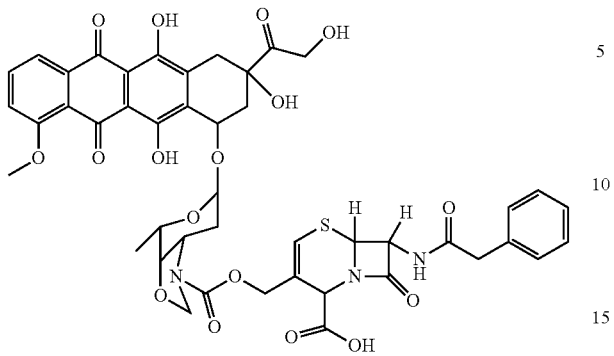
or a pharmaceutically-acceptable salt thereof.
9. A pharmaceutical composition comprising
a. an anthracycline-formaldehyde compound selected from the group consisting of any of the compounds of claims 1, 2, 3, 4, 5, 6, 7 and 8, and
b. a pharmaceutical excipient.
* * * * *

UNITED STATES PATENT AND TRADEMARK OFFICE
CERTIFICATE OF CORRECTION

PATENT NO. : 8,404,650 B2  Page 1 of 1
APPLICATION NO. : 12/091321
DATED : March 26, 2013
INVENTOR(S) : Koch et al.

It is certified that error appears in the above-identified patent and that said Letters Patent is hereby corrected as shown below:

In the Claims:

In Claim 1, Col. 33, line 35, please delete the chemical structure:

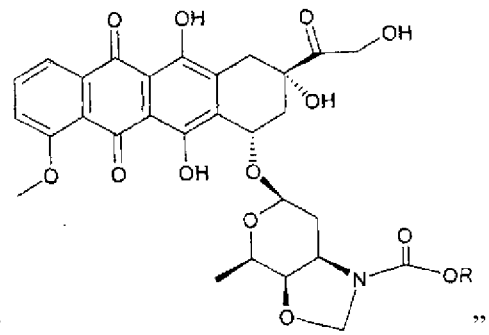

" "

and insert the chemical structure:

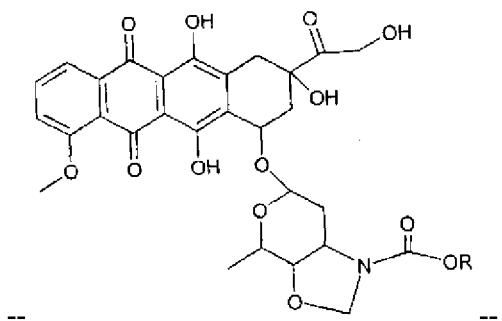

-- --

Signed and Sealed this
Sixth Day of August, 2013

Teresa Stanek Rea
*Acting Director of the United States Patent and Trademark Office*